United States Patent
Yamazaki et al.

(10) Patent No.: US 6,336,939 B1
(45) Date of Patent: *Jan. 8, 2002

(54) AUXILIARY ARTIFICIAL HEART OF AN EMBEDDED TYPE

(75) Inventors: Kenji Yamazaki, Koganei; Toshio Mori; Haruo Iiyama, both of Chino; Shunichi Yamazaki, Suwa; Nobutaka Ito, Chino; Osami Miyao, Ebina; Masanori Hori, Hatano; Yukio Iwasaki, Suwa; Hitoshi Adachi, Fujimi-Machi; Kouji Higuchi, Shiojiri, all of (JP)

(73) Assignees: Sun Medical Technology Research Corporation, Nagano-ken; NOK Corporation; Seiko Epson Corporation, both of Tokyo, all of (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/469,295

(22) Filed: Dec. 22, 1999

Related U.S. Application Data

(60) Division of application No. 08/603,193, filed on Feb. 20, 1996, now abandoned, which is a continuation-in-part of application No. 08/505,784, filed on Jul. 21, 1995, now abandoned, which is a continuation-in-part of application No. 08/079,817, filed on Jun. 22, 1993, now abandoned.

(30) Foreign Application Priority Data

| Jun. 23, 1992 | (JP) | 4-188813 |
| Dec. 15, 1992 | (JP) | 4-334589 |
| Feb. 19, 1993 | (JP) | 5-30617 |

(51) Int. Cl.$^7$ ................................. A61M 1/10
(52) U.S. Cl. ......................... 623/3.13; 600/16
(58) Field of Search ................... 623/3.1, 3.13, 623/3.15, 3.24, 3.26; 415/109, 110, 112, 900; 600/16

(56) References Cited

U.S. PATENT DOCUMENTS

| 4,704,121 A | * 11/1987 | Moise | 623/3.1 |
| 5,145,333 A | 9/1992 | Smith | |
| 5,147,388 A | * 9/1992 | Yamazaki | 623/3.1 |
| 5,376,114 A | * 12/1994 | Jarvik | 623/3.1 |
| 5,531,789 A | 7/1996 | Yamazaki et al. | |
| 5,755,784 A | 5/1998 | Jarvik | |

* cited by examiner

Primary Examiner—Bruce Snow
(74) Attorney, Agent, or Firm—Nixon & Vanderhye

(57) ABSTRACT

An artificial heart has a driving section, a nozzle section, a pump section for insertion into a ventricle of a human heart, and a sealing section forming a seal for a driving shaft extending from the driving section for driving the pump section. A sealing liquid chamber filled with a sealing liquid is formed around the driving shaft between the sealing mechanism and the driving section. The sealing liquid in the sealing liquid chamber maintains the sealing mechanism in a liquid-tight state and lubricates the sealing mechanism, whereby blood is prevented from entering the driving section. Even if blood happens to enter the driving section, the blood is mixed with the sealing liquid and does not coagulate. Thus, the operation of the artificial heart is not suppressed.

8 Claims, 18 Drawing Sheets

AUXILIARY ARTIFICIAL HEART OF AN EMBEDDED TYPE

RELATED APPLICATIONS

This is a divisional of application Ser. No. 08/603,193, filed Feb. 20, 1996 now abandoned, which is a continuation-in-part of application Ser. No. 08/505,784, filed Jul. 21, 1995, now abandoned, which is a continuation-in-part of application Ser. No. 08/079,817, filed Jun. 22, 1993, now abandoned, the disclosures of which are incorporated herein by reference.

BACKGROUND OF THE INVENTION

1. Field of the Invention

This invention relates to an auxiliary artificial heart of an embedded type, embedded in the left or right ventricle of the heart in a human body, and more particularly to an artificial heart operated at high reliability by preventing body fluids such as blood from adversely entering the artificial heart.

2. Description of the Related Art

Conventional artificial hearts are of the diaphragm type, sack type, axially symmetric type, centrifugal type, of pusher plate type or the like. Each of these conventional artificial hearts delivers blood in place of a human heart or by bypassing it.

Recently, an auxiliary artificial heart has been developed which is embedded in a ventricle of a human heart and has the tip end of a nozzle passing through an aorta valve or the like such that blood is delivered from the ventricle into an aorta through the nozzle. The artificial heart does not suppress any function of the human heart when it is installed in the human heart and it delivers additional blood into the aorta when blood pumped out from the human heart is insufficient. The blood is delivered not only by the artificial heart but also by the pulsing or beating of the human heart. Even if the operation of the artificial heart happens to stop, blood is delivered to the body by beating of the human heart.

Naturally, the volume of the part of the artificial heart which is inserted in a ventricle of the human heart must be smaller than the volume of the human heart when it is fully contracted. Such an artificial heart has a pump body comprising a cylindrical axial-flow pump section, a nozzle section provided on its distal end and a driving section provided on the proximal end of the axial-flow pump section. The cardiac apex of a ventricle of a human heart is cut and a short cylindrical cardiac apex ring is embedded therein. The pump section and the nozzle section are inserted in the ventricle through the cardiac apex ring, and the distal end of the nozzle section is inserted in an aorta through its aorta valve or the like. The driving section which has a large volume is embedded in a portion of the thorax which is outside of the human heart.

The artificial hearts has the following problem in connection with the function of a shaft-sealing mechanism provided between the pump section and the driving section. With the artificial heart, a motor and other elements are housed in the driving section, and the rotor of the pump section is driven via a driving shaft extending from the driving section to the pump section. Blood supplied by systemic blood pressure flows through the pump section. In this arrangement, blood is not allowed to enter the space in the driving section. If blood enters the space defined in the driving section, coagulation of blood occurs and the operation of the motor stops.

It is necessary to provide, between the driving section and the pump section, a sealing mechanism for sealing the driving shaft in a liquid tight state in order to prevent blood from entering the interior of the driving section. Since, however, the artificial heart is embedded in a human body, the artificial heart must be operated for a long time without maintenance. It is not easy with the present technology to provide a shaft-sealing mechanism with which perfect sealing is maintained for a long time.

SUMMARY OF THE INVENTION

The object of this invention is to provide an artificial heart which has a shaft-sealing mechanism for completely preventing blood from entering the interior of a driving section for a long time.

An auxiliary artificial heart according to this invention inserted in a ventricle of a human heart, including a cylindrical cardiac apex ring embedded in the cardiac apex of the human heart by cutting the cardiac apex, and a main body of the artificial heart comprising a cylindrical axial flow pump section inserted in the ventricle of the human heart through the cardiac apex ring, a nozzle section extending outward from the distal end of the pump section through the aorta valve of the human heart and a driving section provided on the proximal end of the pump section and disposed outside (or externally) of the human heart, for driving the pump section through a driving shaft.

Between the driving section and the pump section is provided a sealing mechanism for maintaining the driving shaft in a liquid tight state to prevent blood from entering the interior of the driving section from the pump section. The sealing mechanism defines a sealing liquid chamber surrounding the driving shaft at the driving section and a sealing liquid is filled in the sealing liquid chamber.

According to a preferred embodiment, the sealing liquid includes a physiological sodium chloride solution or an anticoagulant such as heparin, and the sealing liquid chamber communicates with a sealing liquid bag made of flexible material, filled with the sealing liquid and embedded in the human body.

The sealing mechanism is provided with an oil seal made of elastic material, closely fitted on the outer peripheral surface of the driving shaft due to its elastic deformation and forming a lubricating film of the sealing liquid between the peripheral surface of the driving shaft and the oil seal.

The pump section is driven by a motor or the like driving unit housed in the driving section. The pump section sucks blood from a ventricle of a human heart and discharges it into an aorta from the nozzle section of the distal end of the pump section by bypassing the aorta valve or the like. Thus, blood is delivered to the aorta not only by the beating of the human heart but also by means of the artificial heart. The artificial heart supplements any insufficient amount of blood which is not provided by the human heart, whereby it is ensured that the necessary amount of blood can be delivered. The volume of the pump section is smaller than the volume of the ventricle of the human heart when it contracts most so as not to interfere with natural beating of the human heart.

The sealing mechanism prevents blood from entering the driving section from the pump section. In this case, the sealing mechanism defines a sealing liquid chamber at the driving section, and a sealing liquid such as a physiological sodium chloride solution fills the sealing liquid chamber. Sealing and lubrication of the sealing mechanism are ensured by the sealing liquid, and blood is securely prevented from entering the interior of the driving section from the sealing mechanism.

Even if the sealing mechanism is deteriorated and blood enters the mechanism, the blood which has entered the mechanism is mixed with the sealing liquid. Thus, blood is not coagulated and does not prevent the smooth operation of the artificial heart.

In the embodiment, the sealing mechanism is provided with an oil seal which forms a lubricant film of the sealing liquid between the oil seal and the outer peripheral surface of the driving shaft and is elastically closely fitted on the outer peripheral surface of the driving shaft for securely preventing the entrance of blood such that the oil seal is not worn and is durable. The oil seal can be designed such that the lubricant film formed between the oil seal and the outer peripheral surface of the driving shaft delivers blood in only one direction toward the pump section. This structure prevents blood from entering the interior of the driving section.

According to the preferred embodiment, the sealing liquid chamber communicates with the sealing liquid bag embedded in the human thorax or other location. A sealing liquid is supplemented from the sealing liquid bag and thus can be supplied to the sealing liquid chamber for a long time.

In a preferred embodiment, the driving shaft uses a dynamic pressure bearing made of ceramic material operated in the sealing liquid. A coating film is formed between the sliding surfaces due to the dynamic pressure of the sealing liquid, thereby reducing rotational resistance of the bearing and preventing wear, leading to high reliability.

When the driving shaft is rotated, the dynamic pressure bearing generates dynamic pressure. The dynamic pressure provide a liquid seal between the sealing liquid chamber and the driving section. The sealing liquid is thereby prevented from flowing from the sealing liquid chamber into the driving section.

The dynamic pressure bearing, which is mounted on the distal end portion of the driving shaft, supplies the sealing liquid to the oil seal. Hence, the sealing liquid circulates in the artificial heart, preventing foreign bodies from depositing.

In a further preferred embodiment, a metal plating is formed on the outer peripheral surface of the driving shaft. Tetrafluoroethylene and its derivatives are made eutectic in the metal plating film, thereby improving not only lubricating properties between the driving shaft and the oil seal but also durability.

The metal plating film of this kind is water-repellent and is well compatible with the living body. Any component that contacts blood or other body fluid may be covered entirely with such a metal plating film.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

The embodiments of this invention will be described with reference the accompanying drawings.

Figure 1:
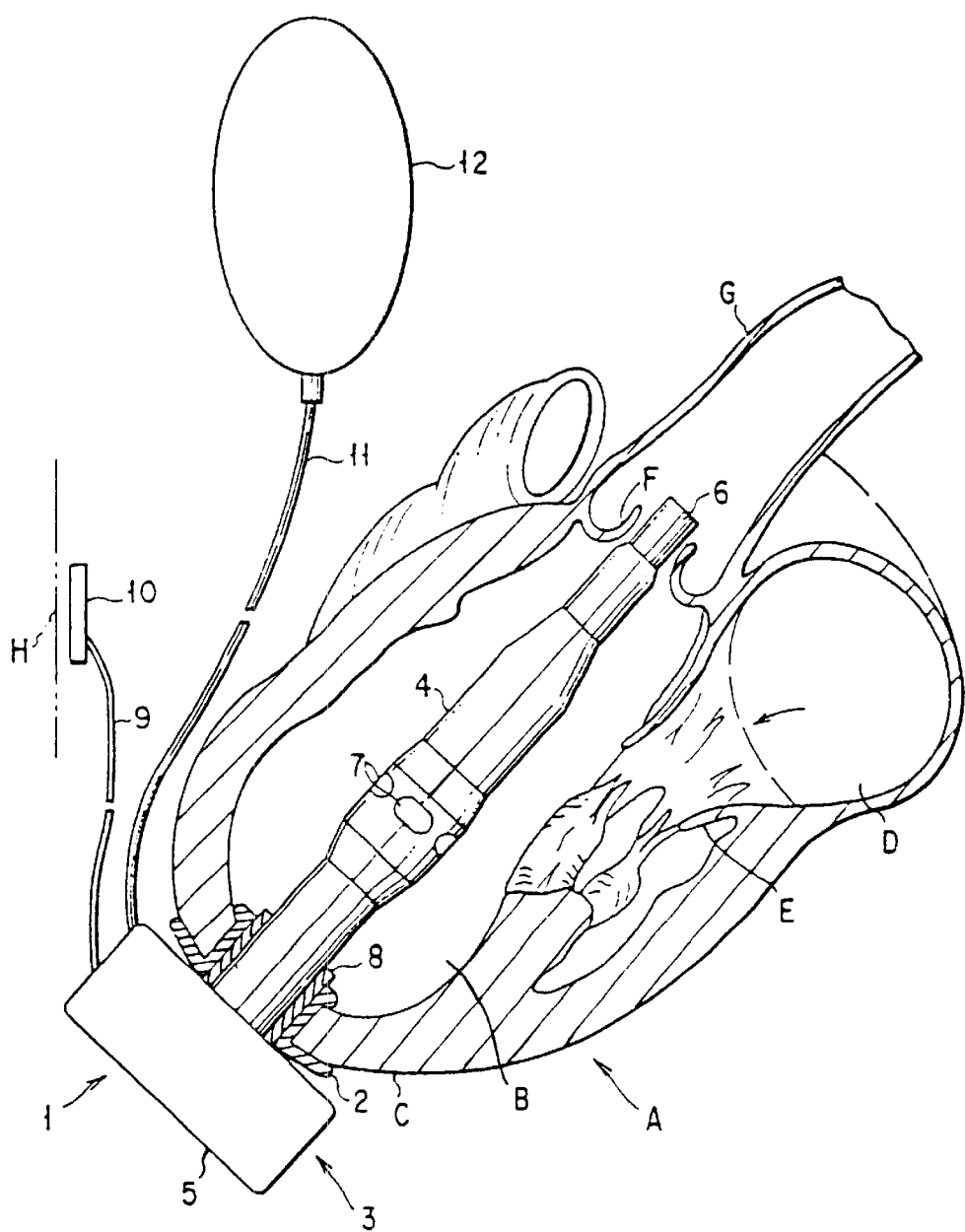
FIG. 1 is a cross-sectional view of an artificial heart of a first embodiment of this invention, provided in the left ventricle of a human heart.

A first embodiment of this invention is shown in FIGS. 1 to 6. FIG. 1 shows an artificial heart of this invention embedded in the left ventricle B of the heart A of a patient (hereinafter referred to as the "human heart"). A cardiac apex, a left atrium, a mitral valve, an aorta valve and an aorta are designated by C, D, E, F and G, respectively.

The artificial heart 1 comprises a cardiac valve ring 2 and the main body 3 of the artificial heart. The cardiac valve ring 2 is a short cylindrical member having a flange and is embedded in the human heart A through the cardiac apex C of the human heart A after the cardiac apex C has been cut. The main body 3 of the artificial heart 1 comprises a pump section 4, a nozzle section 6 provided on the distal end of the pump section 4 and a driving section 5 provided on the proximal end of the pump section 4. The pump section 4 and the nozzle section 6 are inserted in the left ventricle B through the cardiac apex ring 2, and the nozzle section 6 is further inserted in the aorta G through the central portion of the aorta valve F. Liquid tightness is ensured between the cardiac apex ring 2 and the main body 3 by means of a sealing mechanism, for example, a sealing member 8.

The pump section 4 is a relatively small cylindrical member and it has a smaller volume than the volume of the left ventricle B when it contracts most so as not to prevent natural beats of the human heart A. In the pump section 4 is housed a small axial-flow pump which is driven by a motor provided in the driving section 5. The pump section 4 sucks blood from the left ventricle B at a suction port 7 formed in the outer peripheral surface of the section 4 and discharges the blood from the distal end of the nozzle section 6 into the aorta G with the aorta valve F bypassed.

The nozzle section 6 passing through the central portion of the aorta valve F is made of soft synthetic resin material that does not suppress the function of the aorta valve F and it does not injure the aorta valve F.

The driving section 5 is embedded in a portion of the thorax outside of the human heart A. In the driving section 5 are provided a motor and other elements such as electric cells and electronic control elements if they are required. The driving section 5 is connected by means of electric wires 9 to a non-contact type electrode 10 embedded in a portion of the human body close to the patient's skin H. A necessary electric power is supplied from an external electric source (not shown) to the driving section 5 through the electrode 10.

The driving section 5 is further connected to a sealing liquid bag 12 by a flexible tube 11. The sealing liquid bag 12 is made of flexible material and filled with a sealing liquid such as a physiological sodium chloride solution. The sealing liquid bag 12 is embedded in a suitable portion of the body of the patient, such as the thorax or the abdominal cavity.

Figure 2:
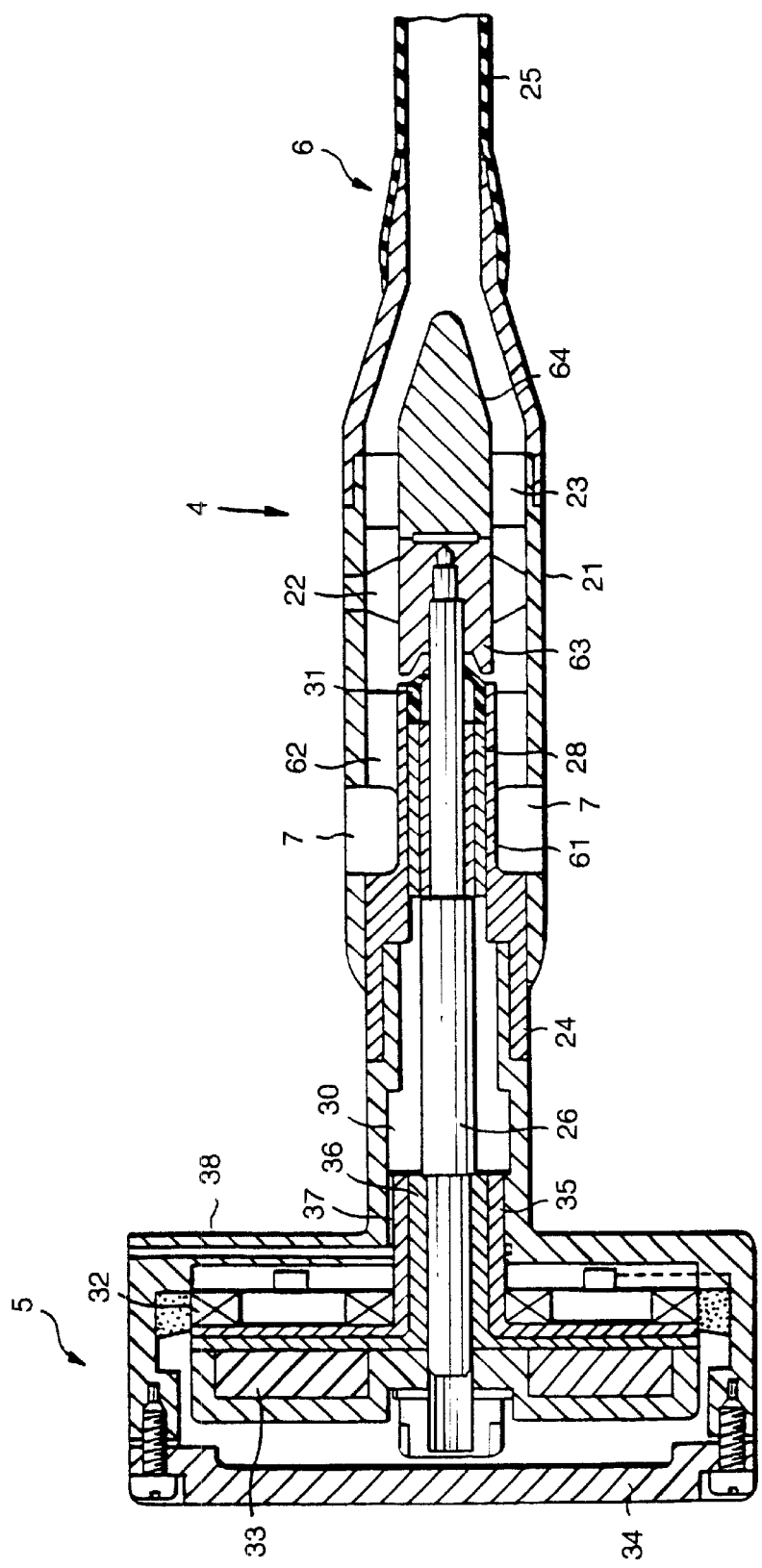
FIG. 2 is a longitudinal cross-sectional view of the main body of the artificial heart of the first embodiment.

The structure of the main body 3 will be described with reference to FIG. 2. The pump section 4 has a cylindrical casing 21 which is reduced in diameter at its distal end portion to form the nozzle section 6 and is connected at its proximal end portion to the driving section 5 by an extension 24. In the casing 21 are provided an axial-flow pump such as a propeller 22 and a plurality of guide vanes 23 for directing the blood flow. The suction port 7 is formed in the outer peripheral surface of the casing 21. In the casing 21 is formed a continuous blood passage extending from the suction port 7 to the nozzle section 6 via the propeller 22 and the guide vanes 23. A thin cylindrical nozzle tube 25 made of flexible synthetic resin material is mounted on the nozzle section 6. As described above, the nozzle tube 25 is designed to improve the contacting properties of the nozzle tube 25 with the ventricle valve F, prevent injury of the ventricle valve F and prevent suppression of the function of the ventricle valve F. The nozzle tube 25 is a flexible thin cylindrical member. Thus, when the artificial heart happens to be out of order, the nozzle tube 25 is collapsed by the blood pressure in the aorta G so as to act as a check valve for preventing blood from flowing backward from the aorta G to the left ventricle B.

The distal end portion of the driving shaft 26 is connected to the propeller 22. The driving shaft 26 passes through the extension 24 and extends to the interior of the driving section 5. In the driving section 5 is provided a motor having a stator coil 32 and a rotor 33. The proximal end portion of the driving shaft 26 is connected to the rotor 33. A cover 34 seals the driving section 5 hermetically.

In this embodiment, the blood flow passage in the pump section 4 is made smooth. The center portion of the pump section 4 has a boss portion 61, in which the driving shaft 26 and the bearing 28 are inserted. The sealing mechanism 31 is located in the distal end of the boss section 61, and has a conical oil seal. The oil seal is fitted in the conical depression formed in the rear end of a propeller boss 63 of the propeller 22, with a small gap formed between the oil seal and the conical depression. The guide vane 23 has a boss 64 which opposes the front end of the propeller boss 63 and is located a short distance therefrom. No steps are made between the inner peripheral surface of the casing 21 and the outer surfaces of the boss section 61, propeller boss 63 and boss 64. A smooth annular blood flow passage is therefore formed between the inner peripheral surface of the casing 21 and the outer surfaces of the components 61, 63 and 64.

The suction port 7 is formed in the proximal part of the boss section 61. A plurality of flow regulating vanes 62 are arranged between the suction port 7 and the propeller 22.

Since the blood flow passage is smooth as described above, the blood can flow smoothly, enhancing the pump's efficiency and reducing the number of places where the blood does not flow. Hence, the possibility of thrombi is decreased.

The distal end portion of the driving shaft 26 is supported by a bearing 28 made of ceramic material, and the proximal end portion of the driving shaft 26 is supported by dynamic pressure bearings 35 and 36 made of ceramic material in the driving section 5. On the distal end portion of the driving shaft 26 is provided a sealing mechanism 31 for performing sealing between the interior of the pump section 4 and the interior of the driving section 5 such that blood in the pump section 4 is prevented from entering the driving section 5.

In the portion of the main body 3 between the sealing mechanism 31 and the driving section 31 (for example, the extension 24 of the casing 21) is formed a sealing liquid chamber 30 surrounding the driving shaft 26. A sealing liquid such as a physiological sodium chloride solution is filled in the sealing liquid chamber 30. If necessary, a blood coagulant such as heparin or any other chemical agents, if required are added to the sodium chloride solution.

The sealing liquid is not limited to physiological chloride solution. Heparin solution may be used as sealing liquid.

An axial groove 37 is formed between the outer wall 38 and dynamic pressure bearing. The space is filled with the sealing liquid and substantially forms part of the sealing liquid chamber 30. Between the outer peripheral surface of the dynamic pressure bearing 35 and the inner peripheral surface of the casing 31 is formed an axial groove 37 which communicates with the sealing liquid chamber 30 and a narrow passage 38 formed in the inside wall of the driving section 5. The sealing liquid chamber 30 communicates with the sealing liquid bag 12 via the groove 37, the passage 38 and the tube 11.

The sealing mechanism 31 will be described. In this embodiment, an oil seal is used as the oil seal 31. The oil seal is made of elastic material such as synthetic rubber, and has an elastically deformable lip portion which abuts against the outer peripheral surface of the driving shaft 26 to maintain liquid tightness. The oil seal has a specific feature in that a lubricating film of the sealing liquid is formed between the oil seal itself and the drive shaft 26. This lubricating film ensures sealing and prevents direct contact of the oil seal with the outer peripheral surface of the driving shaft 26 such that the oil seal is free from wear for a long time.

Figure 3:
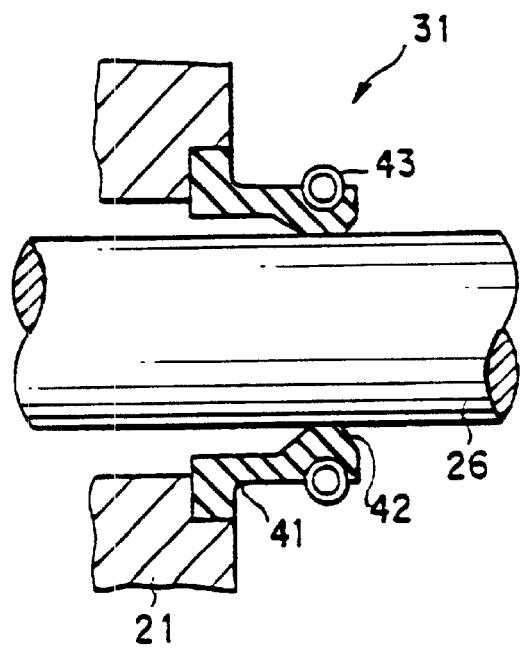
FIG. 3 is a cross-sectional view of a sealing section.

In FIG. 3 is shown an preferred embodiment of the seal mechanism 31 provided with an oil seal 41 made of synthetic rubber, for example, and having a elastically deformable lip portion 42. The inner peripheral surface of the lip portion 42 is in contact with the outer peripheral surface of the driving shaft 26. A garter spring 43 is provided on the oil seal, for stabilizing contact pressure between the lip portion 42 and the outer peripheral surface of the driving shaft 26. As described above, the oil seal 42 is designed such that a thin lubricating film of the sealing liquid is formed between the inner peripheral surface of the lip portion 42 and the outer peripheral surface of the driving shaft 26. The sealing liquid acting as the lubricating film is adapted to circulate on the sealing surface by the rotation of the driving shaft 26. Further, in this embodiment, the sealing liquid acting as the lubricating film is adapted to flow in only one direction toward the pump section 4 so that the sealing liquid flows little by little through the pump section 4. This behavior of the sealing liquid securely prevents blood from entering, from the pump section 4, the sealing surface defined between the oil seal 41 and the driving shaft 26.

Since the sealing liquid is a sodium chloride solution and a very small amount of the solution flows into the pump section 4, it does not affect the human body. It is sufficient that the amount of the flowing-out sealing liquid is several cubic centimeters per month, for example, and the amount of the sealing liquid corresponding to the discharged amount is supplied from the sealing liquid bag 12. When, therefore, several to ten cubic centimeters of the sealing liquid is contained in the sealing liquid bag 12, it is unnecessary to supplement the sealing liquid for more than a year.

The oil seal 41 may be made of various materials. Examples of the materials are: silicone rubber, urethane rubber, ethylene-propylene rubber, nitrile rubber, fluororubber, acrylic rubber, natural rubber, fluororesin, polytetrafluoroethylene, polyurethane, and the like.

A coating is formed on the outer peripheral surface of the driving shaft 26 in order to improve lubricating properties between the oil seal 41 and the driving shaft 26 and enhancing durability. The coating will be described with reference to FIG. 4.

The oil seal 41 is elastically closely fitted on the outer peripheral surface of the driving shaft 26 to prevent blood entrance. Surface treatment is required on the driving shaft 26 so as to maintain the sealing function of the oil seal 41 for a long time. This is because the driving shaft 26 also needs to have good lubricating properties, wear-resistance, and durability. In this embodiment, a compound plating film 52 is formed on the surface of the driving shaft 26. The compound plating film 52 is formed by making a great number of tetrafluoroethylene fine particles 51 distributed evenly in an electroless nickel plating film so as to be eutectic. In the embodiment, the eutectic amount of tetrafluoroethylene is about 25%.

Figure 4:
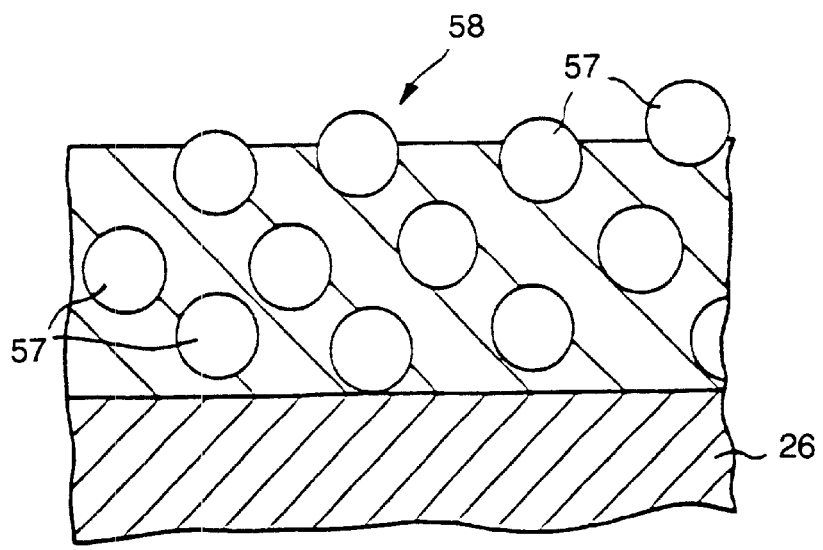
FIG. 4 is an enlarged cross-sectional view showing the structure of a film formed on the outer peripheral surface of a driving shaft.

The driving shaft 26 is made of stainless steel, for example. After cleaning (or removing oily material) and activating, nickel is flush-plated on the driving shaft 26. Thereafter, a nickel-plated film having a thickness of several micrometers is formed in a nickel-phosphorus plating solution in which there are distributed tetrafluoroethylene fine particles which have been made hydrophilic by a surface active agent. By this treatment, fine particles 57 of tetrafluoroethylene are made eutectic in the nickel plating film, and a compound plating film 58 is formed as shown in FIG. 4.

When the base material of the driving shaft 26 is hardened by heat treatment, the compound plating film 52 provides Vickers hardness of 500 to 600. Since fine particles 57 of tetrafluoroethylene are exposed on the surface of the compound plating film 58, they provide good lubricating properties and water-repellent properties. Fine particles 57 of tetrafluoroethylene is suited for human bodies well. The fine particles 57 are held in the nickel plating film and are combined together. Thus, the fine particles 57 are held firmly so as not to fall off the plating film.

The compound plating film 58 is water-repellent, prevents coagulation of blood, and is compatible with the living body. The film 58 may be formed not only on the outer peripheral surface of the driving shaft 26 which contacts the oil seal 41, but also on the other components of the artificial heart which contact blood and/or other body fluids.

The sealing mechanism 31 is not limited to an oil seal but can be applicable to the other sealing mechanism such as a labyrinth packing, if the conditions allow.

Figure 5:
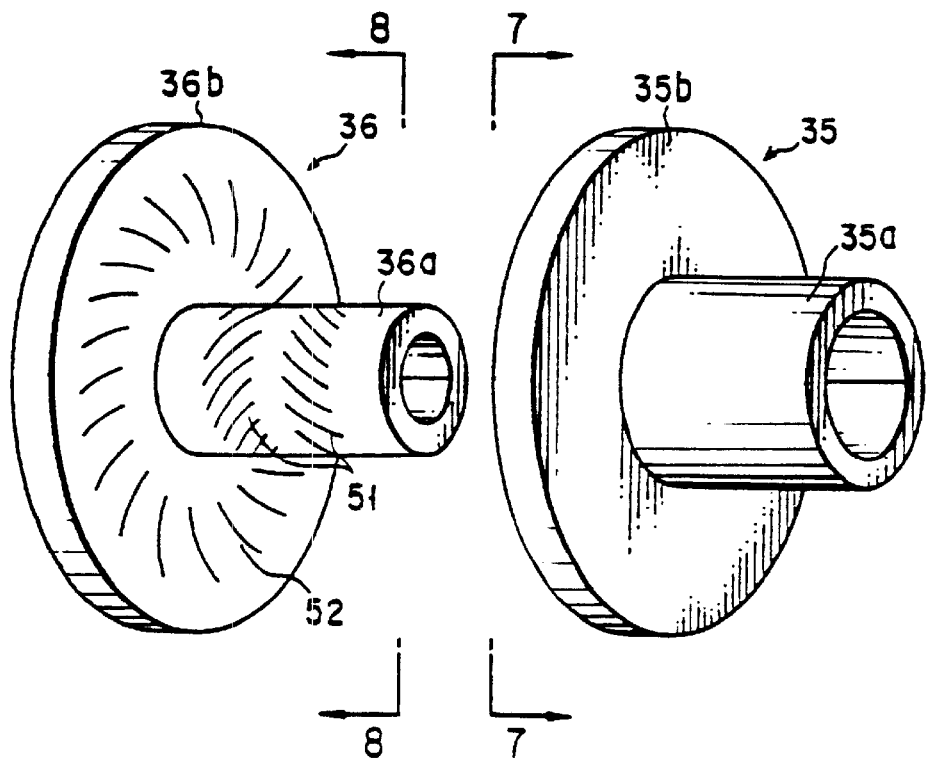
FIG. 5 is an exploded view of one of two dynamic pressure bearings.

A dynamic pressure bearing assembly will be described with reference to FIG. 5. The dynamic pressure bearing assembly rotatably supports the proximal end portion of the driving shaft 26 and performs sealing between the sealing liquid chamber 30 and the space in the driving section 5, as well.

The dynamic pressure bearing assembly comprises an outer fixed-side bearing 35 and an inner rotary-side bearing 36 which are made of ceramic material. The fixed-side bearing 35 and the rotary-side bearing 36 have cylindrical portions 35a and 36a and flange portions 35b and 36b, respectively. The cylindrical portion 36a of the rotary-side bearing 36 is closely fitted in the cylindrical portion 35a of the fixed-side bearing 35, and the flange portions 35a and 35b are in a close contact with each other.

A plurality of dynamic-pressure generating grooves 51 and 52 are formed in the outer peripheral surface of the cylindrical portion 36a of the rotary-side bearing 36 and the contacting surface of its flange portion 36b.

Figure 7:
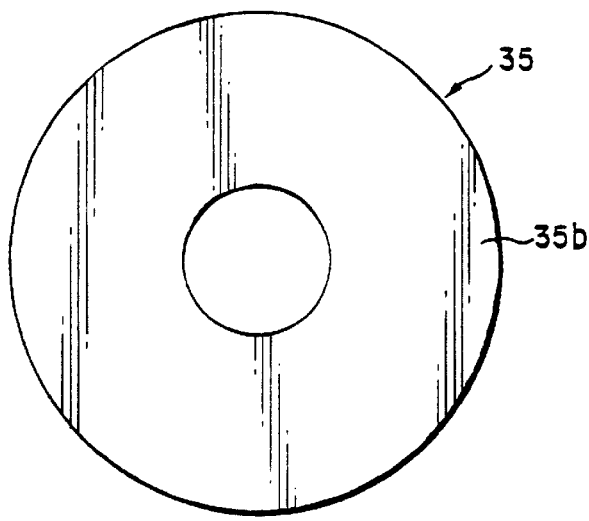
FIG. 7 is a diagram showing the dynamic pressure bearing, as viewed in the direction of arrows 7 in FIG. 5.
Figure 8:
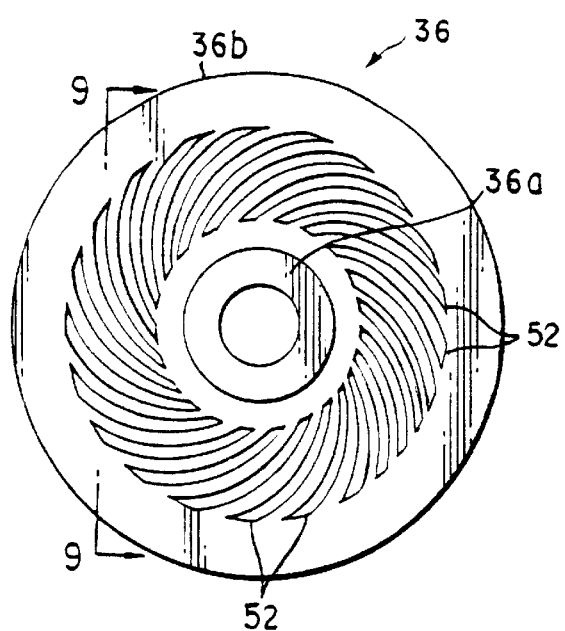
FIG. 8 is a diagram showing the dynamic pressure bearing, as viewed in the direction of arrows 8 in FIG. 5.
Figure 9:
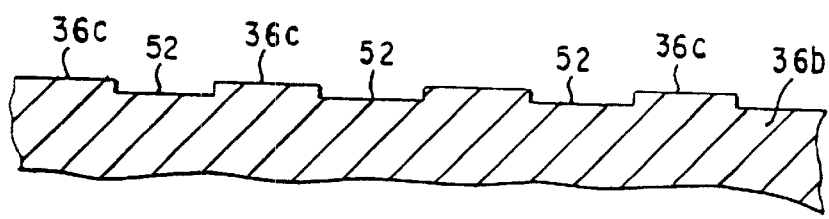
FIG. 9 is a sectional view taken along line 9 in FIG. 8.

The abutting surface of the flange portion 35b of the fixed-side bearing 35 is flat as illustrated in FIG. 7. A plurality of dynamic-pressure generating grooves 52 are formed in the abutting surface of the flange portion 46b of the rotary-side bearing 36 as shown in FIG. 8. The grooves 52 are curved as shown in FIG. 8. They are shallow as illustrated in FIG. 9, about 3 to 10 microns deep. Those portions of the surface, or the lands 36c located among the grooves 52, and the surface of the flange portion 35b of the fixed-side bearing 35 is smooth, having undulation of 0.3 microns or less and maximum roughness of about 0.1 micron. The dynamic-pressure generating grooves 52 have been formed by shot blasting the abutting surface of the flange portion 46b.

A pair of dynamic-pressure generating grooves 51 are formed in the outer peripheral surface of the cylindrical portion 36a of the rotary-side bearing 36. These grooves 51 are shaped like a herringbone and have the same depth as the dynamic-pressure generating grooves 52 formed in the abutting surface of the flange portion 46b. The grooves 51 extend in the opposite directions. Hence, when the driving shaft 26 is rotated, they guide the sealing liquid in the opposite directions.

The operation of the dynamic pressure bearings 35 and 36 will be described.

When the driving shaft 25 is rotated, the rotary side bearing 36 is rotated, too. The sealing liquid is thereby is supplied from the dynamic-pressure generating grooves 52 toward the center of the flange portion 36b, guided along the dynamic-pressure generating grooves 51 formed in the abutting surface of the flange portion 36b. The sealing liquid is simultaneously supplied to the middle portion of the cylindrical portion 36a, also along the dynamic-pressure generating grooves 51.

As a result, a layer of sealing liquid is formed under high pressure at the center of the flange portion 36b. Located between the fixed-side bearing 35 and the rotary-side bearing 36, the sealing liquid layer prevents a mechanical contact between the bearings 35 and 36. It serves as lubricant, enabling the rotary-side bearing 36 to rotate with an extremely low resistance applied to it, and preventing wear of the bearing 36. The cylindrical portion 36a and flange portion 36b of the rotary-side bearing 36 bear the radial load and thrust load exerted by the driving shaft 26, respectively.

Since the dynamic-pressure generating grooves 51 and 52 guide the sealing liquid under high pressure to the center of the flange portion 36b and the middle portion of the cylindrical portion 36a, the liquid reliably serves as lubricant though the liquid itself has poor lubrication action.

Both the fixed-side bearing 35 and the rotary-side bearing 36 are made of a hard ceramic material such as sintered SiC, sintered α-SiC containing BeO, or sintered $Si_3N_4$. The ceramic materials exemplified are very hard and have a small coefficient of friction. No wear occurs between the bearings 35 and 36 even if they directly contact each other when the motor is started or stopped or while the motor shaft is rotating.

Figure 6:
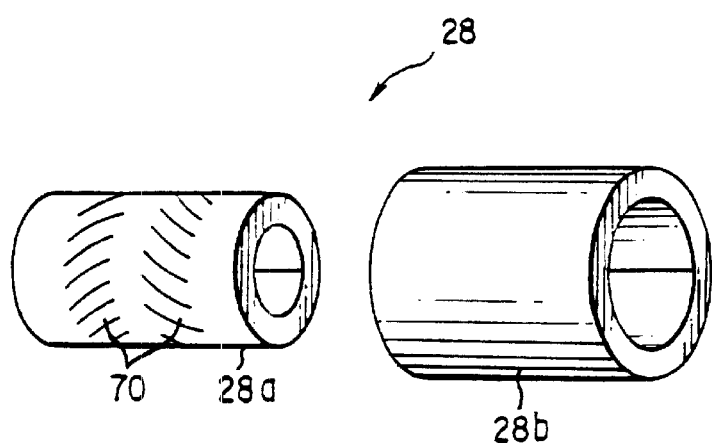
FIG. 6 is an exploded perspective view of the other dynamic pressure bearing.

In FIG. 6 is shown the bearing 28 which comprises a rotary-side bearing 28a and a fixed-side bearing 28b. A pair of dynamic-pressure grooves 70 similar to the dynamic-pressure grooves 51 are formed in the outer peripheral surface of the rotary-side bearing 28a. By the paired dynamic-pressure grooves 70, the sealing liquid is delivered in the opposite directions and a sealing liquid film is formed between the outer peripheral surface of the rotary-side bearing 28a and the inner peripheral surface of the fixed-side bearing 28b. The sealing liquid film reduces resistance of rotation, prevents wear and improves durability.

Figure 10:
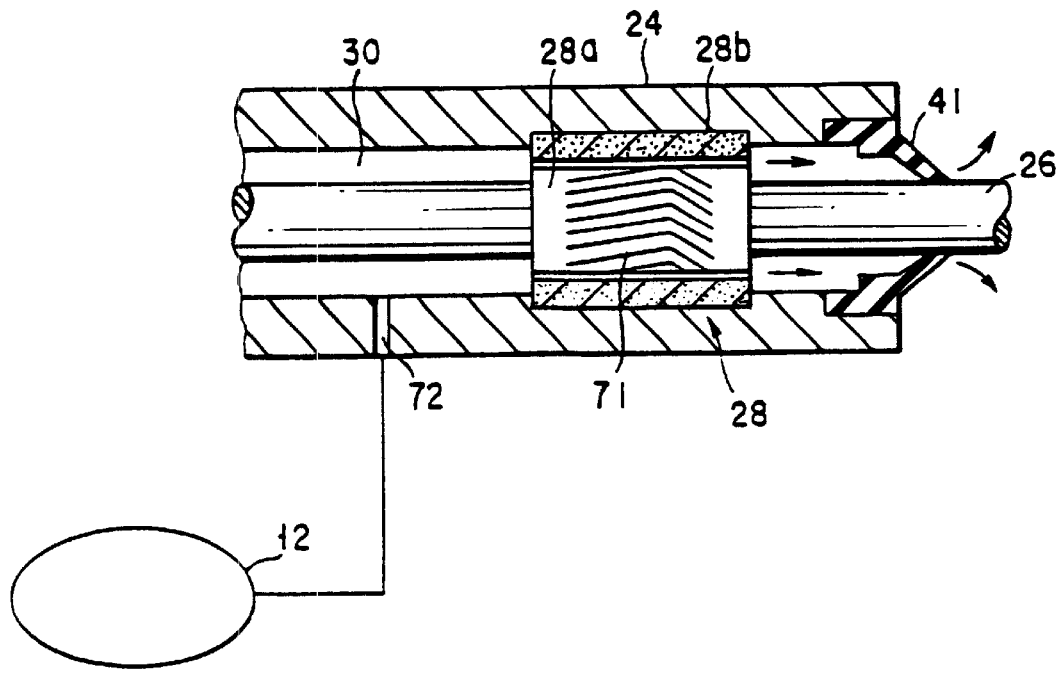
FIG. 10 is a longitudinal cross-sectional view of another embodiment of the dynamic bearing.

The bearing 28 may have a structure as shown in FIG. 10. A plurality of dynamic-pressure generating grooves 71 are formed in the outer peripheral surface of the rotary-side bearing 28a. Each of these grooves 71 consists of two herringbone-shaped grooves 71a and 71b which extend in different directions. The groove 71a is longer than the groove 71b. The dynamic pressure generated in the dynamic-pressure generating grooves 71 forms a sealing liquid film between the rotary-side bearing 28a and the fixed-side bearing 28b and delivers the sealing liquid toward the oil seal 41. The delivered sealing liquid leaks little by little from between the oil seal 41 and the driving shaft 26 so as to prevent blood from entering the driving section.

Therefore, the bearing 28 functions not only as a bearing but also as a micropump for supplying the sealing liquid to the oil seal in tiny amounts.

Figure 11:
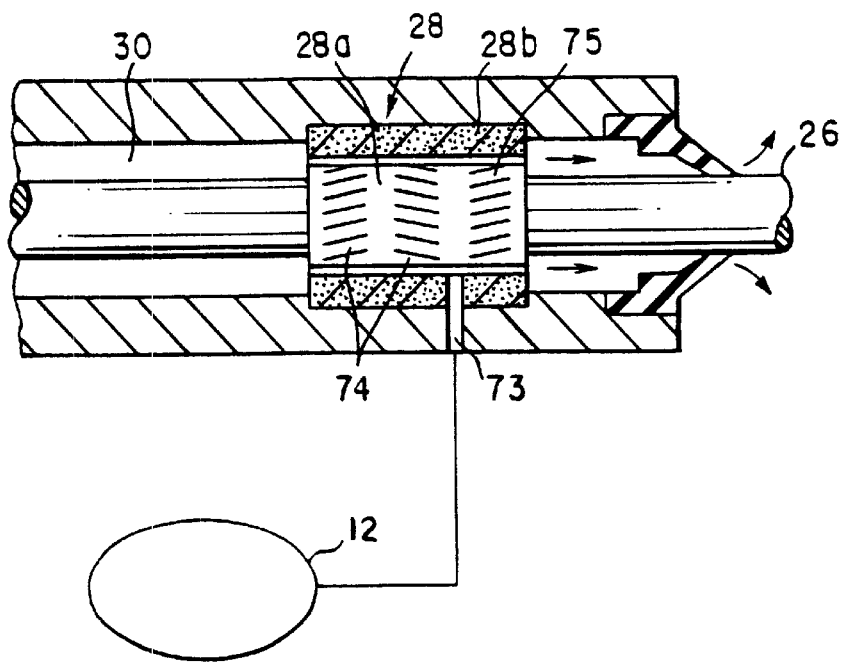
FIG. 11 is a longitudinal cross-sectional view of a further embodiment of the dynamic bearing.

In FIG. 11 is shown another embodiment of the bearing 28 formed in its outer surface with a pair of groups of dynamic-pressure generating grooves and a series of dynamic-pressure generating grooves 75. The paired groups of dynamic-pressure generating grooves 74 deliver sealing liquid in the opposite directions to form a sealing liquid film between the rotary-side bearing 28a and the fixed-side bearing 28b. The dynamic-pressure generating grooves 75 act to deliver the sealing liquid toward the oil seal 41. The sealing liquid is supplied from the supply port 73 to the portion between the dynamic-pressure generating grooves 74 and 75.

Figure 12:
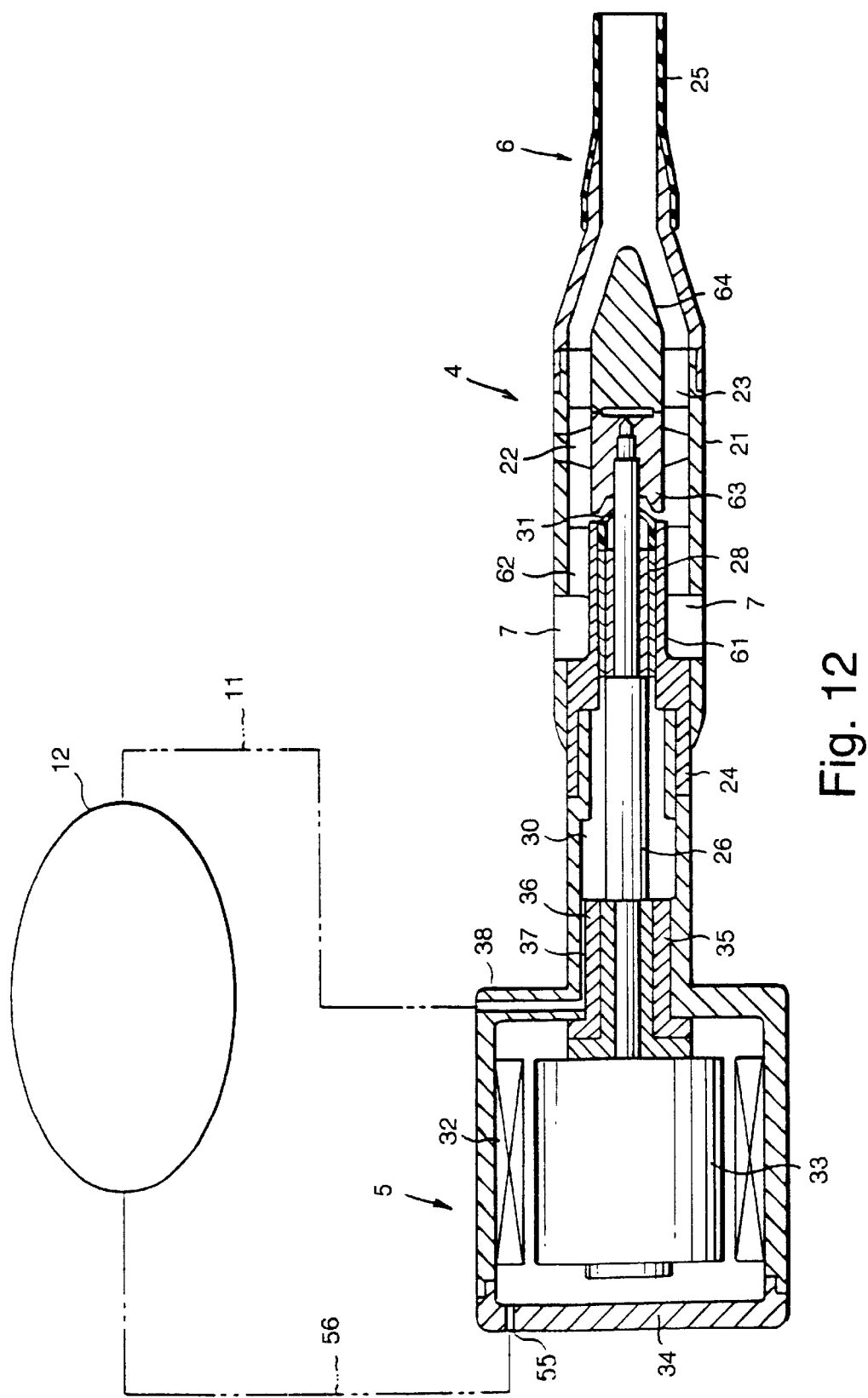
FIG. 12 is a longitudinal cross-sectional view of the main body of an artificial heart of a second embodiment according to this invention.

A second embodiment of this invention will be described with reference to FIG. 12. The motor housed in the driving section 5 in this embodiment is of an immersed type in a liquid so as to circulate a sealing liquid.

The space in the driving section 5 in this embodiment is filled with the sealing liquid, and the stator 32 and the rotor 33 of the motor are immersed in the sealing liquid. In the proximal end portion of the driving section 5 is formed a passage 55 which is connected to a sealing liquid bag 12 via a pipe 56. In this embodiment, the dynamic pressure bearings 35 and 36 do not perform sealing but act as pumps for supplying the sealing liquid in the driving section 5 toward the sealing liquid chamber 30.

In this embodiment, the sealing liquid circulates by the pump action due to the dynamic pressure generated by the dynamic pressure bearings 35 and 36 in such a manner that the sealing liquid is supplied from the interior of the driving section 5 to the sealing liquid chamber 30 then to the sealing liquid bag 12 through the groove 37, the passage 38 and the pipe 11 and returns to the interior of the driving section 5 through the pipe 56 and the passage 55.

Since the interior of the driving section 5 of this embodiment is filled with the sealing liquid, motor resistance increases. However, it is unnecessary to consider damage if the sealing liquid enters the driving section 5 in this embodiment as it does in the first embodiment, leading to an easy design and enhancing reliability. Because of the circulation of the sealing liquid, the liquid carries heat generated in the stator coil 32 of the motor or the like to the sealing liquid bag such that the heat can be dissipated in the human body in a dispersed manner. Thus, the temperature of the sealing liquid and the driving section 5 is maintained substantially as high as the temperature of the human body. It is unnecessary, therefore, to consider the possibility of low-temperature damage even if the temperature of the surface of the driving section 5 rises more than the temperature of the human body. This makes the design consideration for heat radiation of artificial hearts simple and enhances its reliability. The other structures of the second embodiment are the same as those of the first embodiment. The parts and elements of the second embodiment which are the same as those of the first embodiment are designated by the same reference numerals and the description thereof is omitted.

Figure 13:
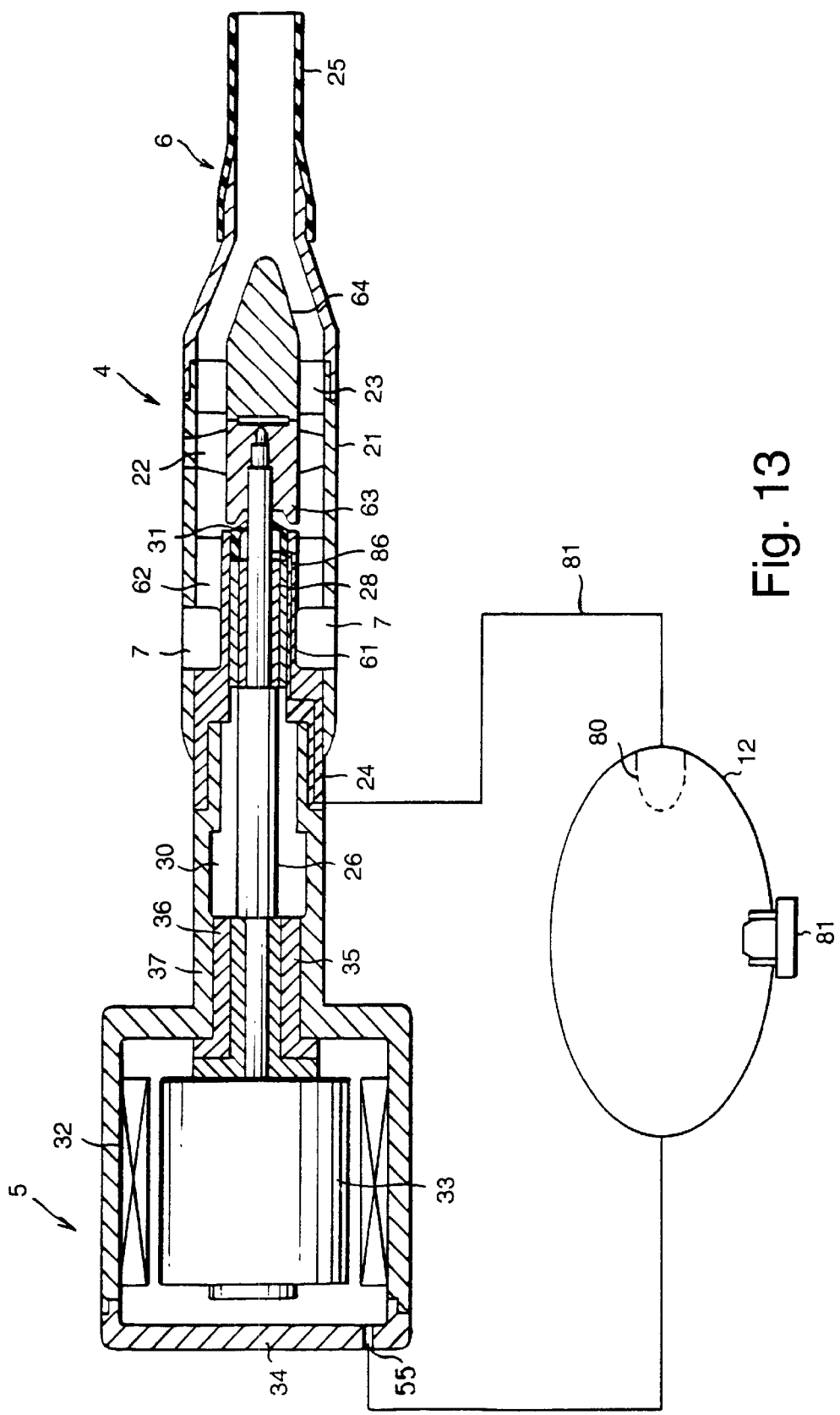
FIG. 13 is a longitudinal cross-sectional view of the main body of the artificial heart of a third embodiment according to this invention.
Figure 14:
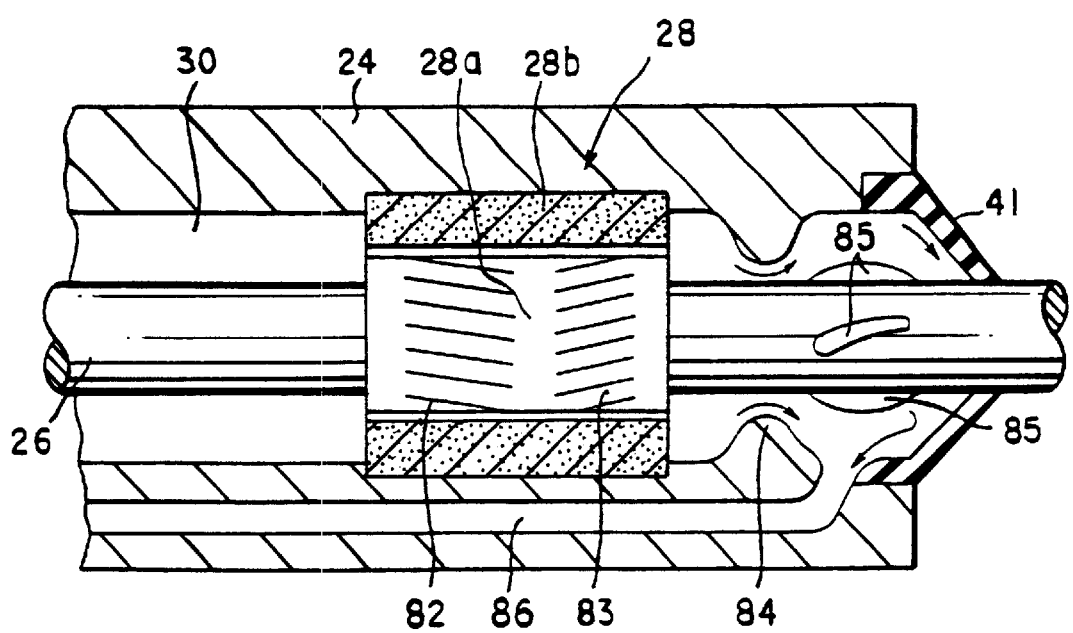
FIG. 14 is an enlarged longitudinal cross-sectional view of part of FIG. 13.

A third embodiment of this invention is shown in FIGS. 13 and 14. Similar to the second embodiment as shown in FIG. 12, the artificial heart of this embodiment circulates a sealing liquid through the main body of the artificial heart and a sealing liquid bag 12. The sealing liquid flows from the supplying port 55 formed in the rear end portion of the driving section 5 into the main body of the artificial heart and then flows out from the vicinity of the sealing mechanism 31 into the sealing liquid bag 12. In this way, the sealing liquid is circulated. In this embodiment, therefore, the sealing liquid circulates in the overall main body of the artificial heart, whereby the interior of the main body is always maintained clean, leading to high reliability.

A filter 80 is provided in the sealing liquid bag 12, for removing foreign matter contained in the sealing liquid returned from the main body of the artificial heart such that the sealing liquid is always clean. The sealing liquid bag 12 is provided with a liquid therapy port 81 through which the sealing liquid is supplemented or replaced.

FIG. 14 is an enlarged partial view of the sealing mechanism 31 of the main body of the artificial heart of this embodiment. A pair of groups of dynamic pressure grooves 82 and 83 are formed in the outer peripheral surface of the rotary-side bearing 28a of the bearing assembly 28. One group of dynamic pressure grooves 82 are longer in the axial direction than the other group of dynamic pressure grooves 83 such that the former group delivers more sealing liquid than the other group. With this structure, therefore, the sealing liquid is sent in opposite directions by the dynamic pressure grooves 82 and 83 and a sealing liquid film is formed between the rotary-side bearing 28a and the fixed-side bearing 28b due to dynamic pressures in the dynamic pressure grooves 82 and 83. Since the former group of dynamic pressure grooves 82 deliver more sealing liquid than the latter group of dynamic pressure grooves 83 do, the sealing liquid is supplied toward the oil seal 41.

When the sealing liquid which is being sent toward the oil seal 41 passes through the orifice portion 84, the flow speed of the liquid increases and is sent to a rear side portion of the oil seal 51. Vane projections 85 are formed on the portion of the driving shaft 26 which is close to the oil seal 41. As the driving shaft 26 rotates, the vane projections 85 agitate the sealing liquid therearound and deliver it to the rear side portion of the oil seal 41. As a result, neither the sealing water nor foreign matter stay in the rear side portion of the oil seal 41, whereby sealing of the oil seal 41 is securely maintained.

In the wall of the extension 24 of the casing 21 of the main body of the artificial heart is formed an exhaust passageway 81 through which the sealing liquid in the rear side portion of the oil seal 41 is sent to the sealing liquid bag 12.

Figure 15:
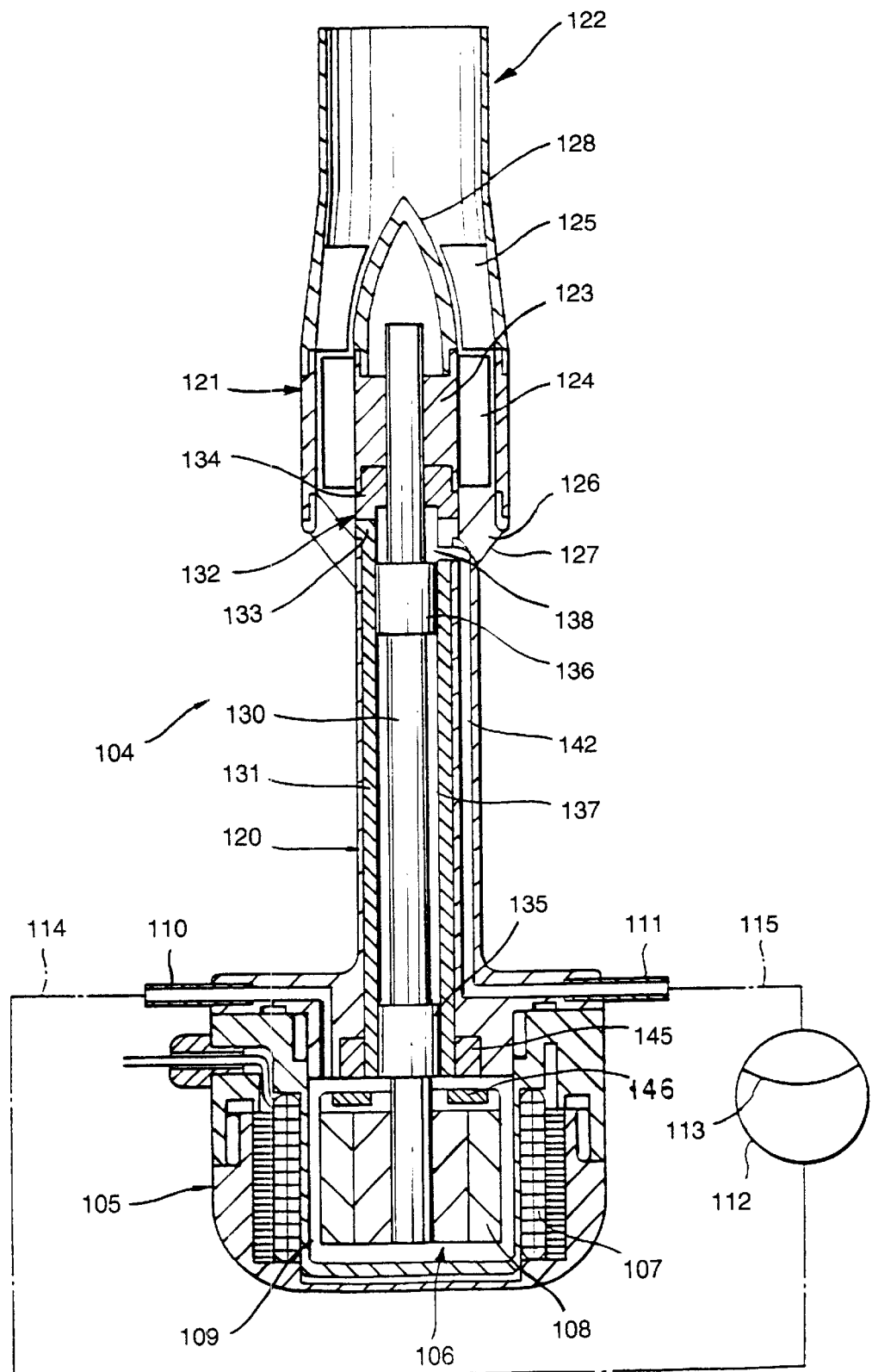
FIG. 15 is a longitudinal cross-sectional view of the main body of an artificial heart according to a further embodiment of the present invention.
Figure 16:
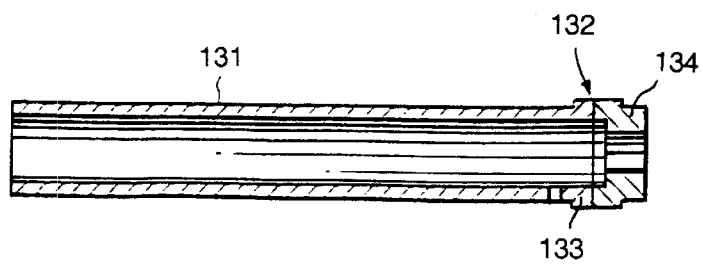
FIG. 16 is a cross-sectional view illustrating the bearing tube, seat ring and follow ring forming part of a sealing mechanism for the embodiment of FIG. 15.
Figure 17:
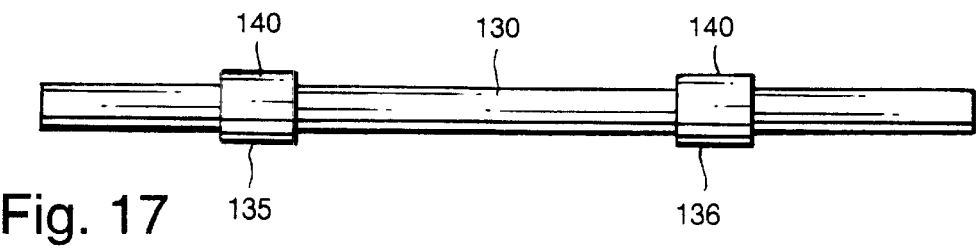
FIG. 17 is an elevational view of the drive shaft and bearings therefor.

In FIGS. 15 to 17, a fourth embodiment of the present invention is shown. In the fourth embodiment, mechanical seals are applied to the sealing mechanism of the driving shaft. While in the previous embodiment, oil seals are used for the sealing mechanism of the driving shaft, the fourth embodiment employs mechanical seals to enhance its durability.

The fourth embodiment is almost the same as the above described embodiment except for the sealing mechanism and its related portions. Specifically, in FIG. 15 numeral 105 indicates a driving section, and 104 denotes a pump section. As in the previous embodiment, the pump section 104 is inserted into the left ventricle B via a cardiac apex ring 2.

In the driving section 105, a motor 106 is provided. The motor 106 is a canned motor where a rotor is housed in a casing filled with liquid. Numeral 107 indicate a stator coil and 108 a rotor the spacing between the rotor 108 and the casing, or an air gap 109 is designed to allow a sealing liquid such as used in the previous embodiment to circulate in the driving section 105, a sealing liquid inlet 110 and a sealing liquid outlet III are made. They are connected to a seal liquid bag 112 via flexible circulation tubes 1–14, 115, respectively. Then, the sealing liquid circulates between the sealing liquid bag 112 and the inside of the artificial heart. In the sealing liquid bag 112, there is provided a filter, which removes foreign matter mixed in the circulating sealing liquid.

The pump section 104 contains a thin-wall, cylindrical tube section 120 and a casing section 121 formed at the tip portion of the tube section. In the casing section 121, a pump rotor composed oil a rotor boss 123 and a plurality of rotor blades 124 provided on the boss so as to project from around the boss is housed. The pump rotor is rotated by the motor 106. Numeral 128 indicates a spinner that provides flow straightening in the casing section 121; there are a plurality of stator vanes 125 and a plurality of front stator vanes also serving as a stay for the casing section 121.

On the base end side of the casing section 121, a fluid inlet 127 is made, through which the blood in the left ventricle of the heart is sucked. The blood is discharged from the distal end of a nozzle section 122. The nozzle section 122 is inserted in the aorta through the aorta valve of the heart.

The number of the stator vanes 125, 126 and that of rotor blades 124 are set at values that do not contain the common factors or integral multiples of the common factors, that is, at prime factors with respect to each other, which thereby prevents the resonance or pulsation of blood sent by rotation of the rotor blades 124.

Explained next will be the driving shaft of the artificial heart and its sealing mechanism in the present embodiment. In FIG. 15, numeral 130 indicates a driving shaft. The base end portion of the driving shaft 130 is connected to the rotor 108 of the motor 106. The tip end portion of the shaft is connected integrally to the rotor boss 123 of the pump rotor, which is driven via the driving shaft 130. In the tube section 120 of the pump section 104, a cylindrical bearing tube 131 is housed. The driving shaft 130 is inserted in the bearing tube 131.

At the tip portion of the bearing tube 131, a mechanical sealing mechanism 132 acting as a sealing mechanism is provided. The mechanical sealing mechanism 132 prevents the blood in the left ventricle of the heart from entering the inside the artificial heart.

The construction of the mechanical sealing mechanism 132 will be described with reference to FIGS. 15 to 17. At the tip portion of the bearing tube 131, a flange-like fixed-side seat ring 133 is formed. The end of the seat ring 133 is machined precisely so as to have a smooth surface perpendicular to the rotation axis of the driving shaft 130 and provides a sealing surface. A rotary-side follow ring 134 is in close contact with the sealing surface of the seat ring 133 so as to rotate freely, thereby maintaining the seal. The follow ring 134 has a disk shape and is provided integrally at the tip portion of the driving shaft 130 so as to be precisely perpendicular to the rotation axis of the driving shaft.

Furthermore, at the base end portion and tip portion of the driving shaft 130, bearing sections 135 and 136 are integrally formed, respectively. These bearing sections 135, 136 are cylindrical and supported by the inner surface of the bearing tube 131 so as to rotate freely. The outer surface of these bearing sections 135, 136 and the inner surface of the bearing tube 131 are machined precisely. These bearing sections 135, 136 and bearing tube 131 support the driving shaft 130 precisely so as to rotate freely.

As shown in FIG. 17, spiral shallow dynamic-pressure grooves 140 are made in the outer surface of these bearing sections 135, 136. These dynamic-pressure grooves 140, when the driving shaft 130 rotates, introduces the sealing liquid into the spacing between the outer surface of these bearing sections 135, 136 and the inner surface of the bearing tube 131, thereby assuring lubrication between them, and allows the sealing liquid to flow toward the tip portion at a specific rate. Therefore, these bearing sections 135, 136 and bearing tube 131 constitute a one-way dynamic-pressure bearing that functions as both a bearing for supporting the driving shaft 130 and a pump for feeding the sealing liquid. Furthermore, the driving shaft 130 is not restricted in the direction of the axis with respect to the bearing tube 131, but can move freely in the axis direction. In the driving section 105, a ring-shaped permanent magnet 146 is provided on the fixed-side of the housing of the driving section. A ring-shaped permanent magnet 146 is also provided on the rotor 108 of the motor 106, that is, on the driving shaft 130 side. These permanent magnets 145, 146 face each other with a specific distance between them. The polarity of these permanent magnets 145, 146 is set so that they may repel one another in the axis direction. The repulsion of these permanent magnets 145, 146 actuates the driving shaft 130 so that the shaft may move toward the base end, thus pressing the follow ring 134 on the driving shaft 130 against the seat ring 133, thereby maintaining the sealing effect of the mechanical sealing mechanism 132.

The spacing between the bearing tube 131 and the driving shaft 1–30 is designed to act as sealing liquid chambers 137, 138 through which the sealing liquid circulates. The sealing liquid chamber 138 is isolated from the outside, that is, the blood passageway in the left ventricle of the heart, by the mechanical sealing mechanism 132, thereby maintaining the seal.

In the outer portion of the tube section 120 of the pump section 104, a circulation passage 142 is made. The tip portion of the circulation passage 142 is connected to the sealing liquid chamber 138 and its base end portion is connected to the sealing liquid outlet 111. Therefore, the sealing liquid flows from the sealing liquid bag 112 through the circulation tube 114 and sealing liquid inlet 110 into the air gap 109 of the motor 106. Then, by the pumping action of the one-way dynamic-pressure bearing composed of the bearing sections 135, 136 and bearing tube 131, the sealing liquid is sent, through the sealing liquid chambers 137, 138 toward the back of the mechanical sealing mechanism 132 at a specific pressure. The sealing liquid fed to the sealing liquid chamber 138 is returned to the sealing liquid bag 112 via the circulation passage 142, sealing liquid outlet 111, circulation tube 115, and filter 113, and circulates in this route.

The function and advantage of the fourth embodiment described above are as follows. First, with the one-way dynamic-pressure bearings 135, 136 feed the sealing liquid to the sealing liquid chamber 138 at a specific pressure. The sealing liquid forms a thin film of 0.5 to 1.0 mm in thickness between the seat ring 133 of the mechanical sealing mechanism 132 and the sealing surface of the follow ring 134. The thin film effects lubrication and sealing between the seat ring and the follow ring. This prevents blood from entering the sealing liquid chamber 138, or the inside of the artificial heart.

When the artificial heart is actually used, protein in the blood, but only a little may enter due to diffusion. This protein is coagulated by heating due to the sliding friction between the seat ring and follow ring that rotate relatively with respect to each other. Particles of the coagulated protein are discharged outward under the influence of the centrifugal force of the follow ring 134 that is rotating, and are washed away by the blood flowing outside the mechanical sealing mechanism. The particles of the coagulated protein are so small that they have no adverse effect on the human body even if diffused into the blood.

Although the coagulated protein may adhere at the inner peripheral edge portions of the seat ring 133 and follow ring 134, such protein particles will be washed away by the sealing liquid circulating inside the mechanical sealing mechanism 134, or inside the sealing liquid chamber 138. These protein particles are captured by the filter 113 in the sealing liquid bag 112, so that the sealing liquid will not be contaminated.

The fourth embodiment using the mechanical sealing mechanism as the sealing mechanism has the following advantages, as compared with the previous embodiment using an oil seal as the sealing mechanism.

Although an oil seal has a simple structure and keeps well in close contact with the driving shaft, when protein in the blood diffuses between the oil seal and the peripheral surface of the driving shaft and coagulates there, the coagulated protein will not be discharged by centrifugal force as described above because the oil seal is in contact with the peripheral surface of the driving shaft. Furthermore, since the oil seal is highly flexible, when coagulated protein deposits between the peripheral surface of the driving shaft and the oil seal, the internal diameter of the oil seal extends easily, increasing the spacing between the peripheral surface of the driving shaft and the oil seal. This increase in the spacing increases the flow rate of the sealing liquid flowing outside through the spacing. The flow of the sealing liquid washes away the coagulated protein into the blood, resulting in an increase in the amount of sealing liquid flowing outside, or the consumption of the sealing liquid. Because of this it is necessary to frequently supply additional sealing liquid to the sealing liquid bag, imposing a heavier burden on the patient.

In contrast, with the mechanical sealing mechanism, centrifugal force discharges the coagulated protein as described earlier, so that the spacing between the seat ring and the follow ring is constantly kept narrow. As a result, the volume of sealing liquid flowing outside is smaller and consequently the frequency of adding the sealing liquid is lower, easing the burden on the patient.

In addition, the sealing liquid circulated as described above cools the mechanical sealing mechanism 132, effectively preventing part of the mechanism from being locally heated to high temperatures due to sliding friction. This prevents the blood cells from being destroyed as a result of the blood touching high-temperature portions.

In addition, a mechanical seal is more durable than the oil seal, because the seat ring and follow ring are made of ceramic material or metal material.

In the above embodiment, the bearing tube 131 and driving shaft 130 defining the mechanical sealing mechanism are preferably formed of fine ceramic material, and the follow ring 134 is formed of graphite material. They are precision ground. The ceramic material is chemically stable and superior in dimensional stability. In the present embodiment, the bearing tube 131 and the seat ring 133 as well as the driving shaft 130 and the bearing sections 135, 136 are formed integrally, so that the dimensional accuracy of their assembly and the resulting mechanical sealing mechanism are high. Consequently, the accuracy of the positional relationship, such as the perpendicularity or concentricity of the seat ring 133 and follow ring 134 with respect to the rotation axis, is high, assuring a high reliability. Since the follow ring 134 is formed of carbon graphite, it matches the seat ring 133 well. Additionally, the graphite, a form of carbon, has self-lubricating properties, and the coefficient of friction is low.

The materials for these members are not restricted to what have been described above, but may be suitable combinations of various types of materials such as ceramic, graphite, composite materials, metal materials, and the like.

In the present embodiment, the follow ring 134 is pressed against the seat ring 133 in the mechanical sealing mechanism 132 by magnetic repulsion of the permanent magnets 145, 146, resulting in a simpler configuration and higher reliability. The urging pressure may come from attraction between the permanent magnets.

Figure 19:
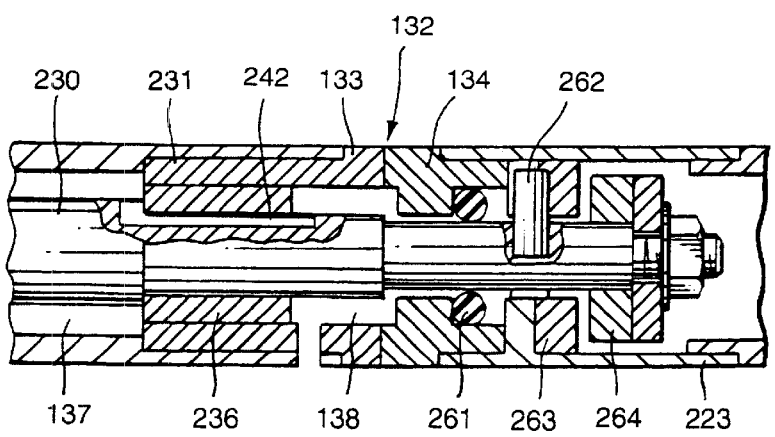
FIG. 19 is a fragmentary longitudinal cross-sectional view of the sealing mechanism of the embodiment illustrated in FIG. 18.
Figure 18:
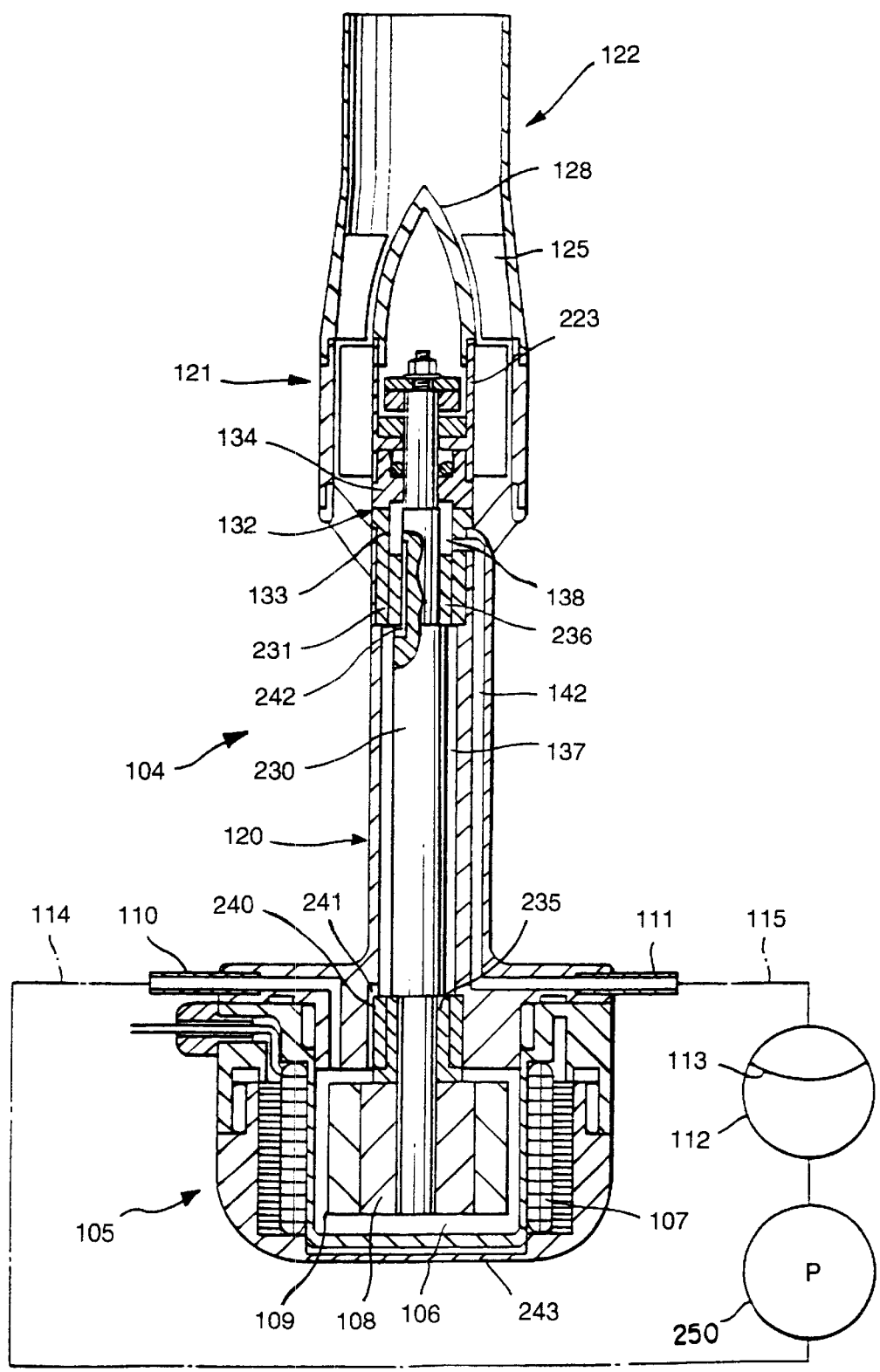
FIG. 18 is a longitudinal cross-sectional view of a main body of an artificial heart according to a still further embodiment hereof.

FIGS. 18 and 19 show a fifth embodiment of the present invention. The fifth embodiment is the same as the fourth embodiment except for part of the mechanical sealing mechanism and part of the circulation route of the sealing liquid.

Specifically, in the fifth embodiment, a driving shaft 230 and bearing members 235, 236 are formed into separate members. The bearing member 235 on the base end side is supported by a bearing sleeve 240, and the bearing member 236 on the tip end side is supported by a short bearing tube 231. On the bearing member 235 on the base end side, a flange section 243 is formed, thereby constituting a thrust bearing.

Between the outer surface of the bearing sleeve 240 and the housing of the driving section 5, a passageway 241 is formed. A passageway 242 is also formed between the inner surface of the bearing section 236 on the tip end side and the driving shaft 230. The sealing liquid passes through these passageways and circulates through the sealing liquid chambers 137, 138. In the present embodiment, a sealing liquid circulating pump 250 is provided. Outside the body or inside the abdominal cavity of the patient, and the pump 250 circulates the sealing liquid.

At the tip end portion of the bearing tube 231, is an integrally formed flange-like seat ring 133. The follow ring 134 is in close contact with the sealing surface of the end of the seat ring 133. The follow ring 134 is a member separate from the driving shaft 230. The follow ring 134 is installed on the rotor boss 223 of the pump rotor. The rotor boss 223 is designed to move freely a specific distance in the axis direction with respect to the driving shaft 230. The follow ring 134 can move to some extent in the axis and the diameter direction with respect to the driving shaft 230. An O ring provides sealing between the follow ring 134 and the driving shaft 230.

The rotor boss 223 is hollow and houses a pair of disk-shaped permanent magnets 263, 264 in it. One permanent magnet 263 is mounted on the rotor boss 223 and the other permanent magnet 264 is mounted on the driving shaft 230. The polarity of these permanent magnets 263, 264 is set so that they may repel each other. The force of repulsion presses the follow ring 134 against the end of the seat ring 133.

In the present embodiment, the driving shaft 230, rotor boss 233, and follow ring 134 can move independently from each other. A relative movement between them can absorb vibrations caused by their rotation. This enables the follow ring 134 to be pressed against the end of the seat ring 133 more stably, resulting in an increase in the reliability of the mechanical sealing mechanism 132.

In this embodiment, because the sealing liquid is circulated by the sealing liquid circulating pump 250, the circulating flow rate and pressure of the sealing liquid can be regulated freely.

Figure 20:
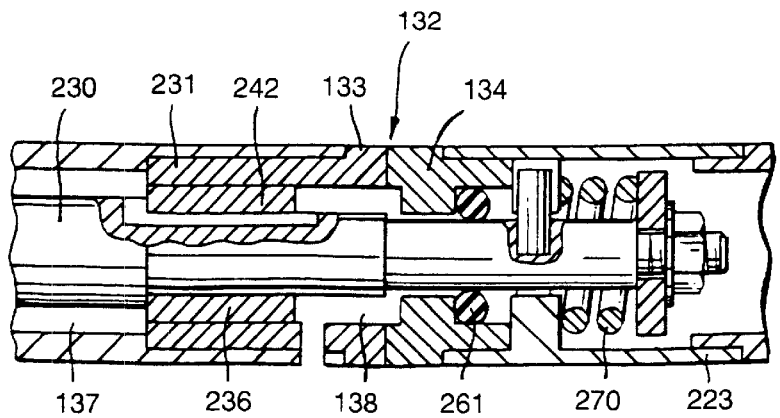
FIG. 20 is a view similar to FIG. 19 illustrating a further form of sealing mechanism.

FIG. 20 shows a sixth embodiment of the present embodiment. In the sixth embodiment, the follow ring 134 is pressed against the seat ring 133 by a compression coil spring 270 in place of the pair of permanent magnets 263, 264 in the fifth embodiment. The sixth embodiment has the same configuration as that of the fifth embodiment except as stated above. In FIG. 20, the parts corresponding to those in the fifth embodiment are indicated by the same reference symbols and explanation of them will not be given.

The present invention can be applied to an artificial heart having a centrifugal pump. Hereinbelow, we will explain embodiments of an artificial heart comprising a pump section consisting of a centrifugal pump and a mechanical seal mechanism.

Figure 21:
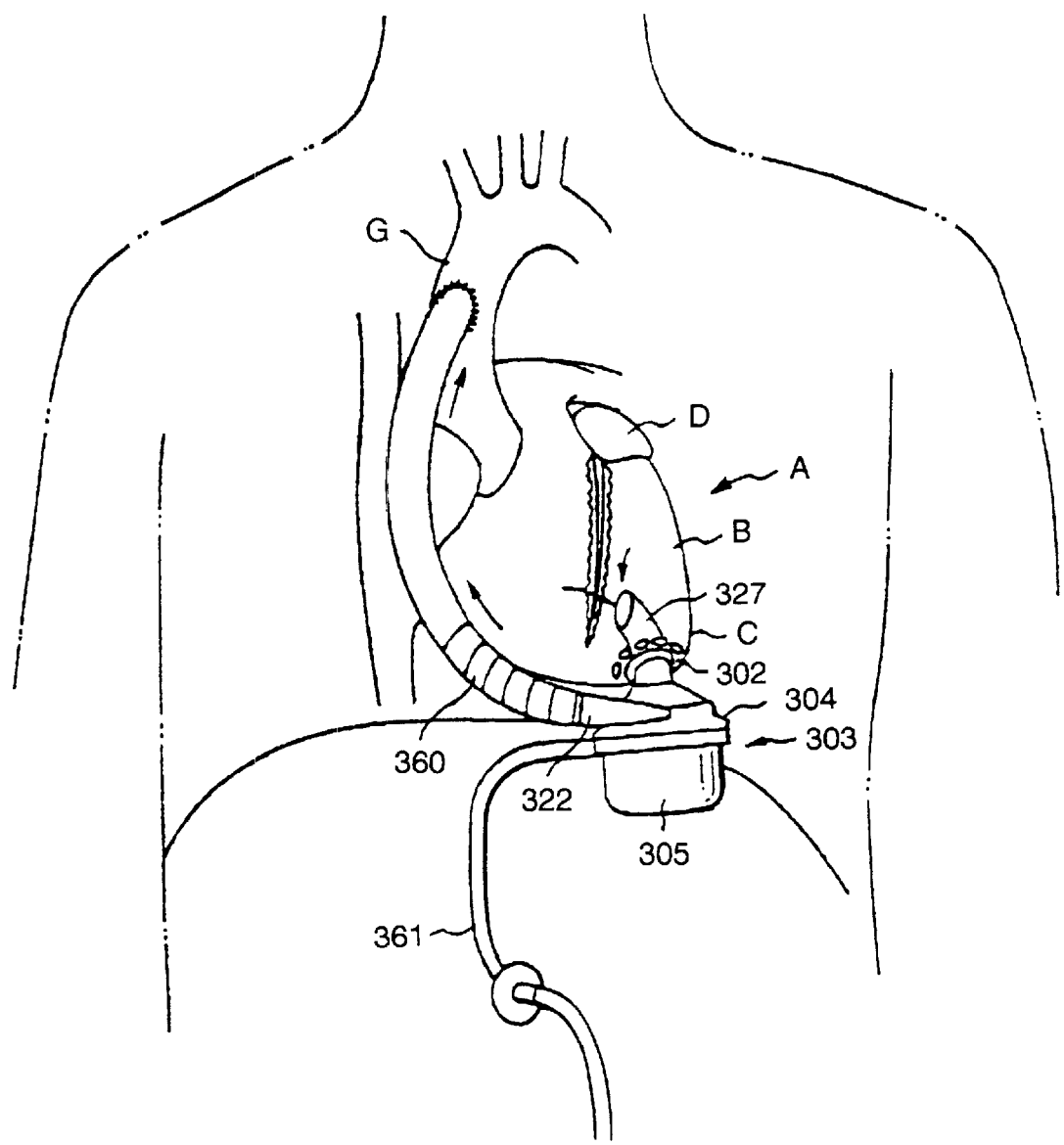
FIG. 21 shows the state of an artificial heart having a centrifugal pump embedded in a body cavity.

FIG. 21 shows the state of an artificial heart having a centrifugal pump embedded in a body cavity. To describe more specifically, the main body 303 of the artificial heart is constituted of a pump section 304 consisting of a centrifugal pump and a driving section 305 accommodating a motor therein. The main body 303 is embedded in the body cavity and on the outside of the heart.

Onto the pump section 304, an entrance nozzle 327 is provided. To cardiac apex C of heart A, a cardiac apex ring 302 is fitted. The entrance nozzle 327 is inserted into a left heart ventricle B by way of the cardiac apex ring 302.

To an exit nozzle 322 of the pump section 304 is connected an artificial blood vessel 360, which is connected to aorta G without passing through the left ventricle B. The artificial vessel 360 is connected to aorta G by suture.

To the main body 303 is connected a supply tube 361, which is guided out of the body cavity via appropriate means, In the supply tube 361 are accommodated a tube for circulating a sealing liquid and an electric wire for driving a driving section 305. The sealing liquid is circulated by way of the main body 303 by a sealing liquid supply unit (not shown). Power is supplied to the driving section from an outside electric source via the electric wire.

In the artificial heart having the aforementioned structure, the blood of the left ventricular B is first sucked by the pump section 304 by way of the entrance nozzle 327, pressurized by the pump section 304, passed through the artificial blood vessel 360 via the exit nozzle 322, and fed into aorta G without passing through the left ventricular B and a mitral valve. The artificial heart serves for supplying blood to aorta G without disturbing the natural heart beat in order to make up for shortage in blood supplied only by the natural heart beat.

Figure 22:
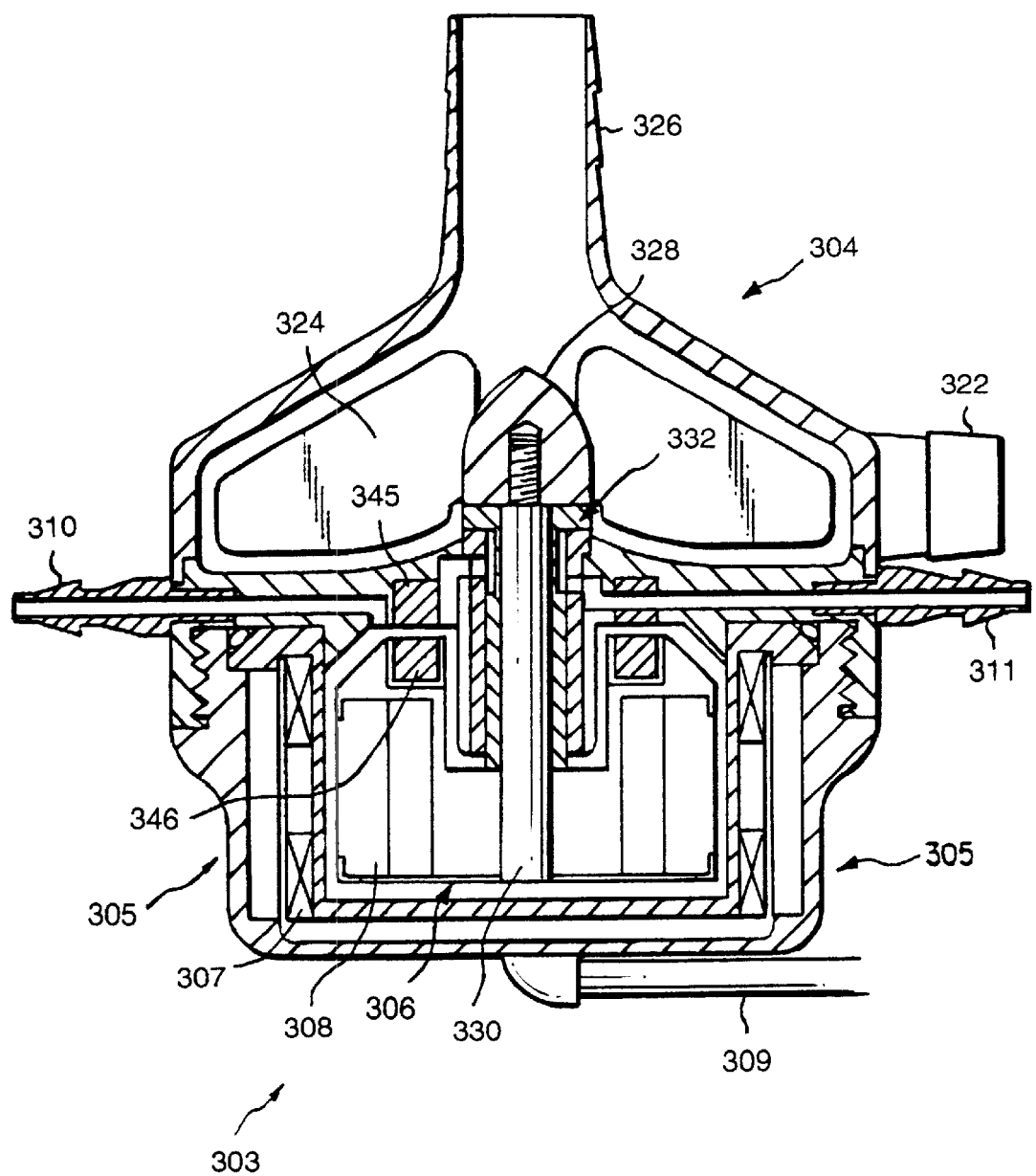
FIG. 22 is a longitudinal cross-sectional view of the main body of the artificial heart of a seventh embodiment.

FIG. 22 shows a main body 303 of the artificial heart having a centrifuge pump according to a seventh embodiment, shown in FIG. 21. The main body 303 is constituted of the pump section 304 consisting of a centrifugal pump and a driving section 305. In the pump section 304, an impeller 324 is provided. A reference numeral 328 indicates a spinner. To the pump section 304 is provided an entrance port 326, to which the entrance nozzle 327 is further provided. The pump section includes an exit port 322, to which an end portion of the artificial vessel 360 is connected.

The driving section 305 houses a motor 306 having an driving shaft 330. The top end portion of the driving shaft 330 is inserted into the pump section 304, thereby being connected to the impeller 324. Reference numerals 307, 308, and 309 are a stator, rotor, and electric wire for supplying power to the motor, respectively.

In the driving portion 305 are disposed a scaling liquid inlet 310 and a sealing liquid outlet 311, by way of which the sealing liquid is circulated through the driving section 305.

To the portion in which the driving shaft 330 is just inserted into the pump section 304 is provided a mechanical seal mechanism 332, which prevents blood passing through the pump section 304 from entering into the driving section 305. To the casing side of the driving section 305 and to the rotor-side of the motor 306, a pair of permanent magnets 345 and 346 are respectively provided so as to be opposed to each other. Attractive force generated between permanent magnets 345 and 346 is loaded on the driving shaft 330 in the lengthwise direction thereof, and consequently the force is added onto a portion between a seat ring and a follow ring of the mechanical seal mechanism 332 in the lengthwise direction, maintaining sealing between these rings. The sealing liquid is circulated through the mechanical seal mechanism 332 to ensure a sealing tightness and simultaneously to cool the mechanical seal mechanism 332.

Figure 23:
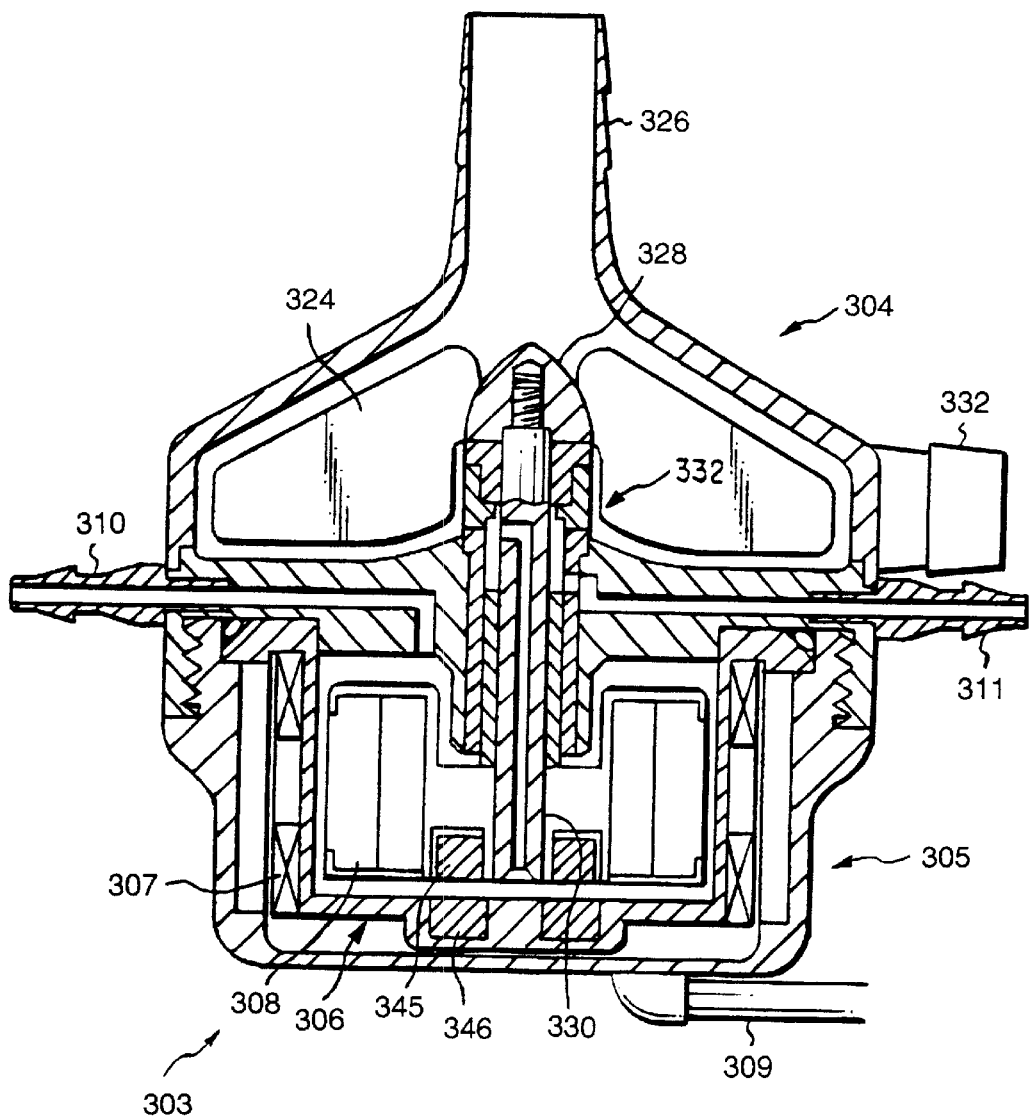
FIG. 23 is a longitudinal cross-sectional view of the main body of the artificial heart of an eighth embodiment.

FIG. 23 shows the main body 303 of the artificial heart of an eighth embodiment of the present invention. The main body of this embodiment has substantially the same structure as that of the seventh embodiment of the present invention except that permanent magnets 345 and 346 are arranged so as to provide load to the driving shaft 330 in the lengthwise direction by repulsion force thereof. To avoid repetitions in FIG. 23, like reference numerals designate like structural elements explained in FIG. 22 showing the seventh embodiment.

Figure 24:
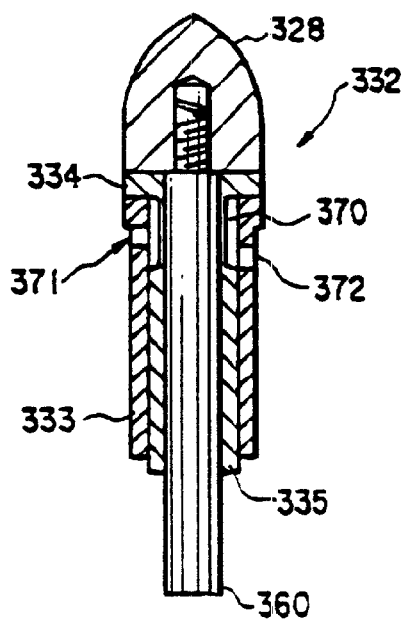
FIG. 24 is a longitudinal cross-sectional view of the mechanism of a ninth embodiment.

FIG. 24 shows the mechanical seal mechanism 332 of a ninth embodiment for use in the artificial hearts having a centrifugal pump of the seventh and eighth embodiments. The mechanical seal mechanism 332 is characterized in that a follow ring 334 of a flange form is provided onto the top of a driving shaft 360 and in that a cylindrical shaft bearing section 335 is formed so as to be integrated with the follow ring 334. Furthermore, the periphery of the integrated structure is covered with a cylindrical seat ring 333, which is provided to the casing of the driving section 305 and the like. The upper surface of the seat ring 333 is tightly connected to the lower surface of the follow ring 334, thereby constructing the mechanical seal mechanism. The inner periphery of the seat ring 333 supports the seat bearing section 335 in such a way that the section 335 can be rotated freely in this way, the seat bearing mechanism is constructed.

Between the seat ring 333 and the shaft bearing section 335 is formed a sealing liquid passage 370 of a ring-form. On the lateral side of the seat ring 333 is formed a sealing liquid flow-in port 371. On the opposite side of the flow-in port 371 is formed a sealing liquid flow-out port 372.

In the mechanical seal mechanism of the embodiment 8, the seat ring 333 is made of a ceramic material. On the other hand, the follow ring 334 and the shaft bearing section 335 are made of a carbon composite material.

The sealing liquid circulating through the driving section 305 is supplied from the sealing liquid flow-in port 371 into the sealing liquid passage 370, flows through the passage 370, and goes out from the sealing liquid flow-out port 372. The flow of the sealing liquid ensures the sealing tightness between the seat ring 333 and the follow ring 334, thus preventing blood of the pump section 304 from flowing into the driving section 305. On the other hand, the flow of the sealing liquid cools the seat ring 333 and the follow ring 334, thus preventing temperature elevation taken place in the sealing portion. Successful suppression of temperature elevation makes it possible to prevent coagulation of blood proteins taken place in a narrow interspace of the sealing portion. As a result, the sealing tightness is ensured and the seat ring 333 is prevented from adhering to the follow ring 334.

To prevent coagulation of blood proteins as mentioned above, it is effective to reduce the temperature of a lubricating thin film of the sealing liquid to 50° C. or less which is present between the seat ring 333 and the follow ring 334. This is because if the temperature of the lubricant thin film is suppressed to 50° C., or less, the coagulation of blood components in the space between the seat ring 333 and the follow ring 334 can be securely prevented since the most coagulation-susceptible component of the blood, namely, fibrinogen, is denatured by heat of about 50° C.

The temperature can be reduced by controlling the flow amount of the sealing liquid flowing through the sealing liquid passage 370. If an excessive amount of the sealing liquid is used, the sealing liquid passing through the sealing portion and flowing into the pump section 304 is increased in amount. As a result, the sealing liquid will be consumed in a large amount and should be supplied more frequently. This result is not preferable since a patient receives a great burden, For the reasons mentioned above, it is important to set the flow amount of the sealing liquid at a minimum and sufficient amount required for controlling the temperature of the lubricating thin film to 50° C. or less.

In practice, it may be preferred to perform a test using an artificial heart and determine the minimum and sufficient amount of the sealing liquid based on the experimental results obtained in the test. Since the artificial heart is embedded in a body when used, the peripheral temperature of the artificial heart is equal to the body temperature. It will be therefore easy to determine the minimum and sufficient flow amount to be needed if the experiment can be carried out under temperature as constant as the body temperature.

If the sealing portion between the seat ring 333 and the follow ring 334 can he further cooled by a different method other than the aforementioned cooling method employing a sealing liquid, the minimum and necessary flow amount can be set to a further smaller value. For example, it is effective to increase surface area to be exposed to the sealing liquid or blood by making the sealing surface in the form of flange. Alternatively, the following method is effective. The spinner 328 is formed solid by using highly heat conductive metal material and brought into contact with the upper surface of the follow ring 334. If the spinner 328 thus constructed is used, heat can be released into blood through the spinner 328 by means of heat conduction.

There are various preferable embodiments of mechanical seal mechanism 332 other than those introduced in the above. In a tenth embodiment of the mechanical seal mechanism 332 shown in FIG. 25, a follow ring 334 is formed independently of the shaft bearing section 335. The sealing liquid passage 373 surrounding the driving shaft 360 is formed therebetween. The follow ring 334 may be formed of a material different from that forming the shaft bearing section 335. For example, the follow ring 334 is formed of a carbon composite material to impart lubricity and to ensure sealing tightness; on the other hand, the shaft bearing section 335 is formed of a ceramic material to improve durability. The tenth embodiment has the same structure as that of the ninth embodiment shown in FIG. 9 except for the aforementioned respects. To avoid repetitions in FIG. 25, like reference numerals designate like structural elements explained in FIG. 24 showing the ninth embodiment.

Figure 26:
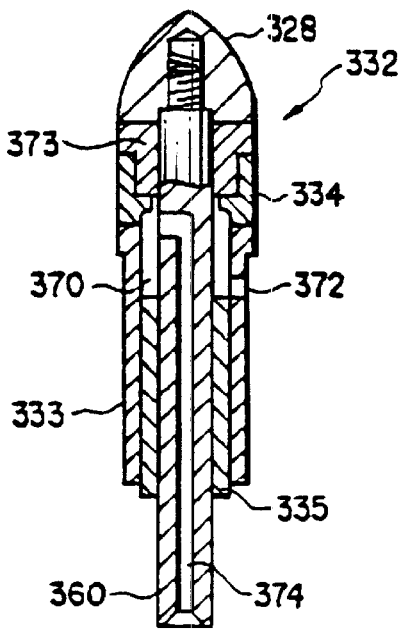

In an eleventh embodiment of the mechanical seal mechanism 332 shown in FIG. 26, between a follow ring 334 and a spinner 32 is interposed a bumping material 373 formed of elastic material, e.g., ethylene propylene diene monomer (EPDM). The follow ring 334 is capable of moving in the lengthwise direction and diameter direction of a driving shaft 360. By virtue of this structure, if the driving shaft 360 is vibrated, the vibration will be adsorbed by the bumping material 373, preventing the vibration of transmitting to the follow ring 373. In this mechanism, the follow ring 334 can be connected tightly and securely to a seat ring 333, ensuring sealing tightness.

In the eleventh embodiment, a sealing-liquid introducing passage 374 is formed in the center portion of the driving shaft 360 along the lengthwise direction. The sealing-liquid introducing passage 374 is opened in the periphery surface to communicate with a sealing liquid passage 370. The sealing liquid therefore blows out from the opening of the sealing liquid introducing passage 374, and impinges upon the sealing portion of the follow ring 334 and the seat ring 333. on the other hand, the sealing liquid is turned around in the sealing liquid passage 374 when a rotation shaft 360 is rotated. By virtue of these structural features, the sealing portion can be efficiently cooled.

Figure 25:
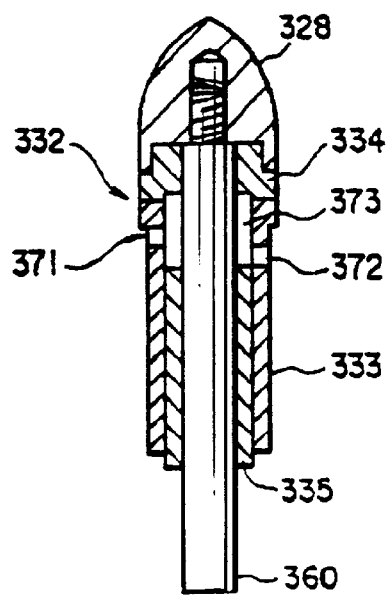
FIG. 25 is a longitudinal cross-sectional view of the mechanism of a tenth embodiment; a longitudinal cross-sectional view of the FIG. 26 is a longitudinal cross-sectional view of the mechanical seal mechanism of an eleventh embodiment.

The eleventh embodiment has the same structure as that of the tenth embodiment except for the aforementioned respects. To avoid repetitions in FIG. 26, like reference numerals designate like structural elements explained in FIG. 25 showing the tenth embodiment.

Figure 27:
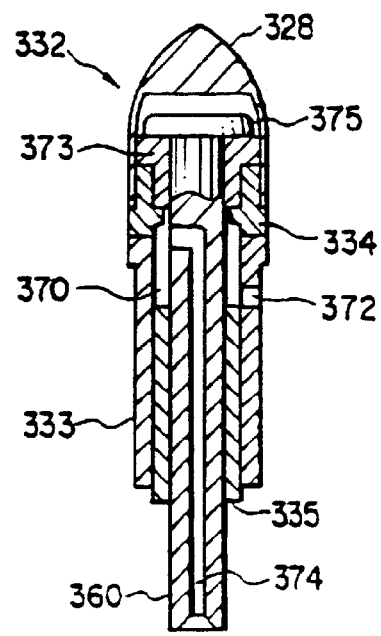
FIG. 27 is a longitudinal cross-sectional view of the mechanical seal mechanism of a twelfth embodiment.

In the twelfth embodiment of the mechanical seal mechanism shown In FIG. 27, a head section 375 is provided onto the top of a driving section 360. A bumping material 373 is interposed between the head section 375 and a follow ring 334. The twelfth embodiment has the same structure as that of the eleventh embodiment except for the aforementioned respects. To avoid repetitions in FIG. 27, like reference numerals designate like structural elements explained in FIG. 26 showing the eleventh embodiment.

The mechanical seal mechanisms according to the ninth to twelfth embodiments respectively shown in FIGS. 24 to 27 are suitable for the sealing mechanism for an artificial heart having a centrifugal pumps as described in the seventh and eighth embodiments shown in FIGS. 22 and 23. Furthermore, application of these mechanical seal mechanisms may not be limited to the artificial heart having a centrifugal pump. The mechanical seal mechanisms may be, of course, applied to an artificial heart having an axial-flow pump as shown in FIGS. 15 or 18.

Figure 28:
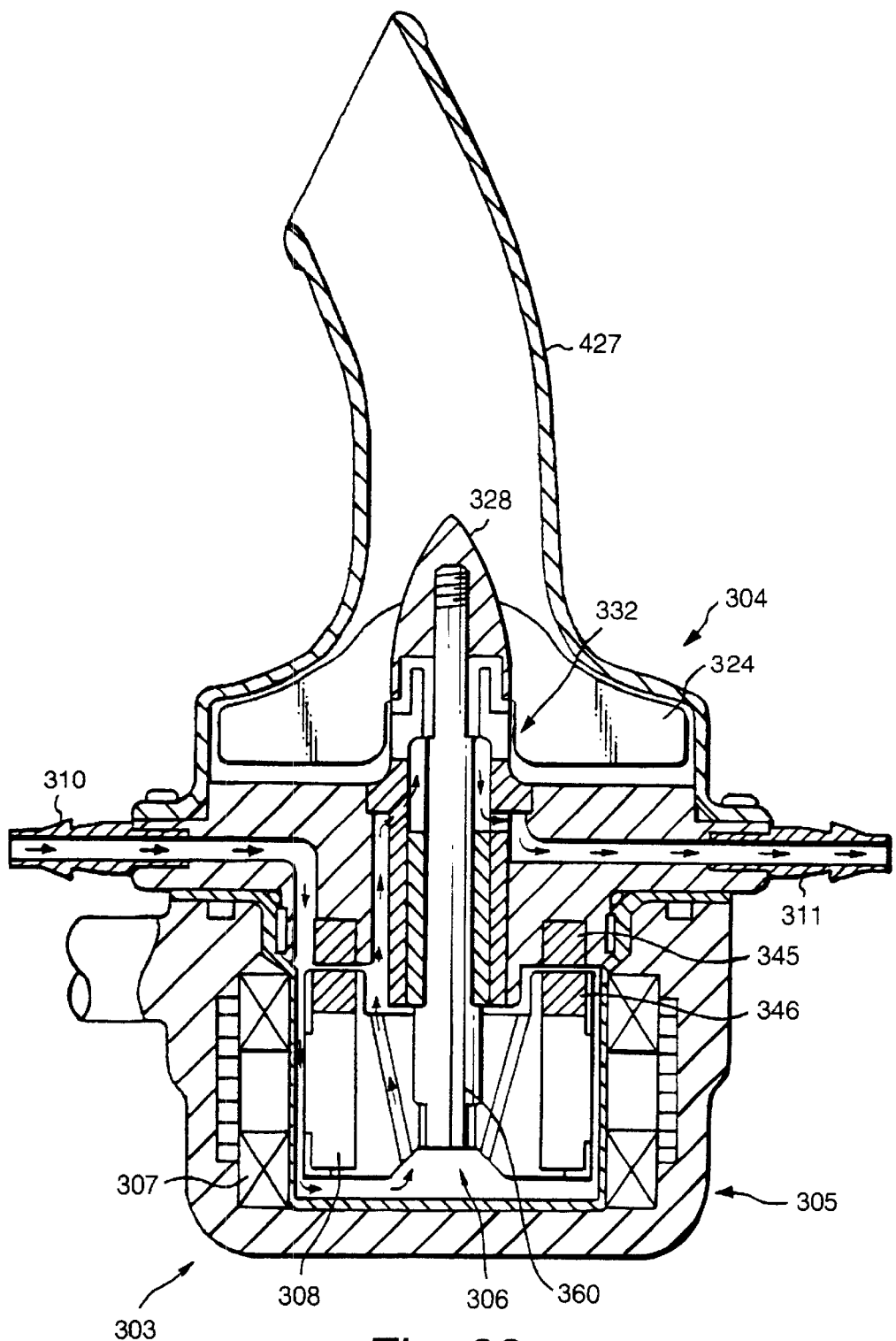
FIG. 28 is a longitudinal cross-sectional view of the main body of the artificial heart of a thirteenth embodiment.

In a thirteenth embodiment of the artificial heart having a centrifugal pump, shown in FIG. 28, a pump section 304 is formed so as to be integrated with an introducing nozzle 427 for introducing blood. The introducing nozzle 427 is bent along the shape of the left ventricle.

Figure 29:
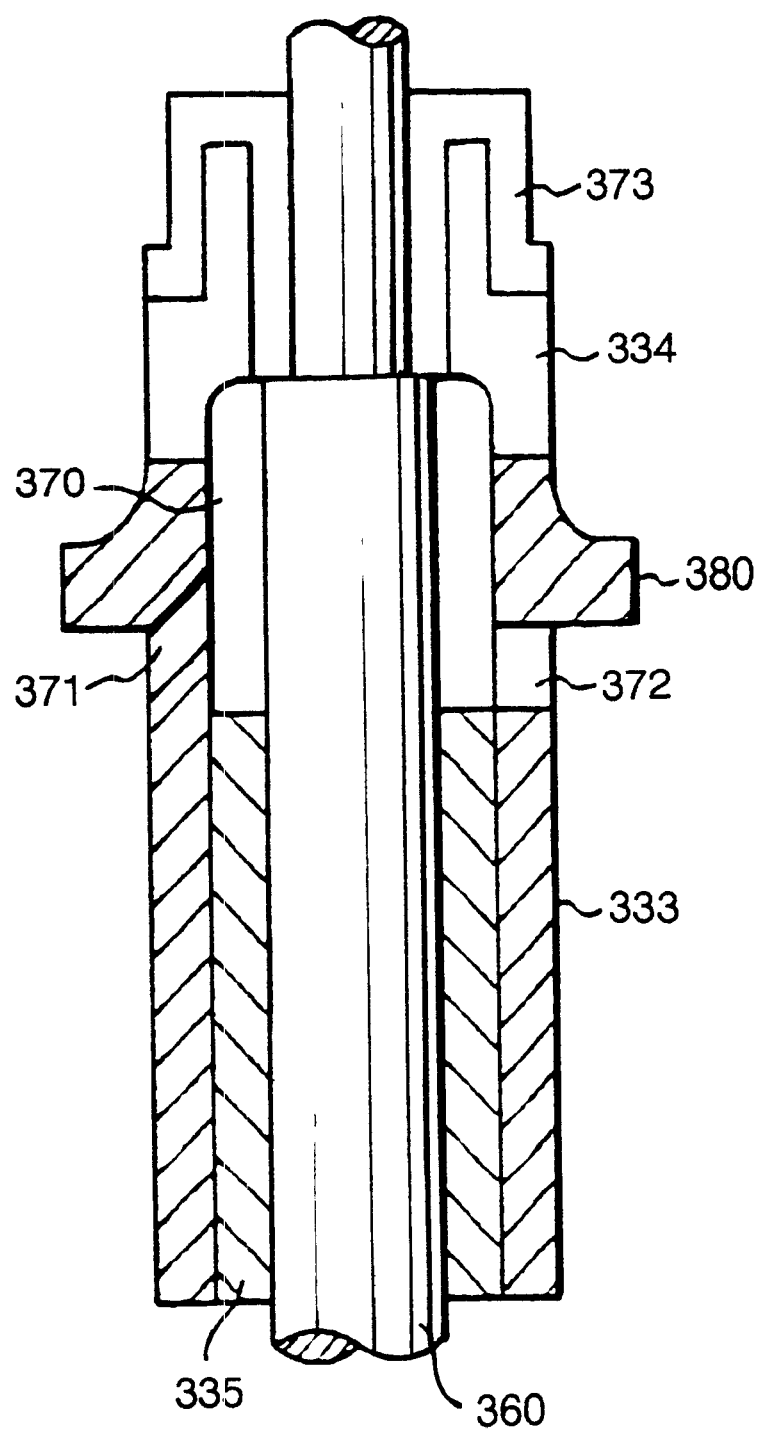
FIG. 29 is a longitudinal cross-sectional view of the mechanical seal mechanism of a fourteenth embodiment.

FIG. 29 shows the structure of a fourteenth embodiment of the mechanical seal mechanism 332 suitable for use in the artificial heart according to the thirteenth embodiment shown in FIG. 28. The fourteenth embodiment employs a bumping material 373 having a cross-section of an inverted U-letter form. The bumping material 373 covers an outer peripheral surface, upper surface and inner peripheral surface of a follow ring 334. Since bumping effect can be improved by the bumping material thus arranged, it is possible to reduce the bumping material 373 in thickness. Consequently, an entire size of the mechanical seal mechanism 332 can be reduced.

In this embodiment, since the seal liquid inlet 371 is opened upwardly in the diagonal direction, a flowing-in sealing liquid is directly hit upon the sealing portion, cooling it more effectively. The fourteenth embodiment has the same structure as that of the tenth embodiment shown in FIG. 25 except for the aforementioned respects. To avoid repetitions in FIG. 29, like reference numerals designate like structural elements explained in FIG. 25 showing the tenth embodiment.

The application of the mechanical seal mechanism according to the fourteenth embodiment shown in FIG. 29 is not limited to the artificial heart having a centrifugal pump mentioned above. It may be, of course, used in the artificial heart having an axial-flow pump mentioned above.

In both the fifth and sixth embodiments of FIGS. 19 and 20, the driving shaft 230 mounts a pin 262 (illustrated only in FIG. 19) which engages a recess in the follower ring 134. Consequently, upon rotation of driving shaft 230, the rotor boss 223 and associated parts including hollow ring 134 rotate in response to rotation of driving shaft 230.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. An artificial heart including a main body, said main body comprising:

(a) a pump section having a proximal end;

(b) a driving section having a driving shaft provided on said proximal end of said pump section for driving said pump section via said driving shaft, said driving shaft having an outer peripheral surface;

(c) a sealing mechanism provided between said driving section and said pump section, for maintaining said driving shaft in a liquid tight state and preventing blood from entering said driving section;

(d) a sealing liquid chamber surrounding said driving shaft between said sealing mechanism and said driving section;

(e) a dynamic-pressure bearing provided on said driving shaft, and a rotational sliding surface formed with spiral dynamic-pressure generating grooves therein, said dynamic-pressure bearing supplying a sealing liquid to said sealing mechanism through said spiral dynamic-pressure generating grooves.

2. The artificial heart according to claim 1, wherein said outer peripheral surface of said driving shaft is covered with a coating film comprising plated metal and fine particles made of tetrafluoroethylene and derivatives thereof distributed in said plated metal.

3. The artificial heart according to claim 1 wherein the surfaces of components which contact blood or other body fluids or both are covered with a coating film comprising plated metal and fine particles of tetrafluoroethylene and derivatives thereof in said plated metal.

4. The artificial heart according to claim 1, further comprising a sealing liquid bag made of flexible material for filling with sealing liquid and embedment in a human body, said sealing liquid chamber being connected to said sealing liquid bag.

5. The artificial heart according to claim 1, wherein said dynamic-pressure bearing is made of ceramic material.

6. The artificial heart according to claim 1, wherein said dynamic-pressure bearing comprises a cylindrical portion having an outer peripheral surface, for receiving radial load, and said dynamic-pressure generating grooves are formed in an outer peripheral surface of the cylindrical portion of said dynamic-pressure seal bearing.

7. The artificial heart according to claim 1, wherein said driving section has an interior for filling with a sealing liquid, and said sealing liquid chamber extends to said interior of said driving section.

8. The artificial heart according to claim 1, wherein said driving shaft has a central axis, and said dynamic-pressure generating grooves are asymmetrical with respect to the central axis of the driving shaft.

* * * * *